(12) United States Patent
Scheurer et al.

(10) Patent No.: US 8,535,269 B2
(45) Date of Patent: Sep. 17, 2013

(54) INSERTION HEAD WITH A NEEDLE PROTECTION IN ITS HANDLE

(75) Inventors: Simon Scheurer, Bern (CH); Christian Thalmann, Kehrsiten (CH)

(73) Assignee: Roche Diagnostics International AG, Rotkreuz (CH)

( * ) Notice: Subject to any disclaimer, the term of this patent is extended or adjusted under 35 U.S.C. 154(b) by 1036 days.

(21) Appl. No.: 12/049,118

(22) Filed: Mar. 14, 2008

(65) Prior Publication Data

US 2008/0208139 A1 Aug. 28, 2008

Related U.S. Application Data

(63) Continuation of application No. PCT/EP2006/005614, filed on Jun. 12, 2006.

(30) Foreign Application Priority Data

Sep. 15, 2005 (EP) .................................. 05 020 157

(51) Int. Cl.
*A61M 5/178* (2006.01)
*A61M 25/00* (2006.01)
*A61M 31/00* (2006.01)

(52) U.S. Cl.
USPC .................... 604/164.01; 604/93.01; 604/263

(58) Field of Classification Search
USPC ................. 604/164.01, 93.01, 263, 174, 177, 604/192, 198, 264, 272, 273, 523
See application file for complete search history.

(56) References Cited

U.S. PATENT DOCUMENTS

2005/0080386 A1 4/2005 Reid

FOREIGN PATENT DOCUMENTS

| CN | 2358841 Y | 1/2000 |
| DE | 198 21 723 | 11/1999 |
| DE | 20 2004 017862 | 11/2004 |
| DE | 203 20 207 | 11/2004 |
| DE | 602 01 121 | 5/2005 |
| DE | 10 2004 039 408 | 3/2006 |
| EP | 0615768 | 9/1994 |
| FR | 2752164 | 2/1998 |
| WO | WO 02/02165 | 1/2002 |
| WO | WO 02/081012 | 10/2002 |
| WO | WO 2004/101071 | 11/2004 |
| WO | WO 2005/046781 | 5/2005 |

OTHER PUBLICATIONS

International Search Report for PCT/EP06/08763, Nov. 27, 2006.
International Search Report for PCT/EP06/05614, Sep. 29, 2006.
International Search Report for PCT/EP06/05615, Oct. 20, 2006.
First Office Action issued Jun. 2, 2010 from Patent Application in China No. 200680033748.5 filed Jun. 12, 2006, on the basis of International Application No. PCT/EP2006/005614, titled Insertionskopf Mit Nadelschutz Im Griff.

*Primary Examiner* — Theodore J Stigell
*Assistant Examiner* — Brooke Matney
(74) *Attorney, Agent, or Firm* — Dinsmore & Shohl, LLP

(57) ABSTRACT

An insertion head for medical or pharmaceutical applications includes a base having a lower side positionable on organic tissue; an insertion means movably mounted by the base and insertable into the tissue; where the insertion means is movable relative to the base from a protective position in which a free end of the insertion means is short of the lower side of the base, into an insertion position in which the free end protrudes beyond the lower side; and a receptacle that is open towards the lower side of the base and that can be detached from the base, and which accommodates at least the free end of the insertion means in its protective position.

37 Claims, 22 Drawing Sheets

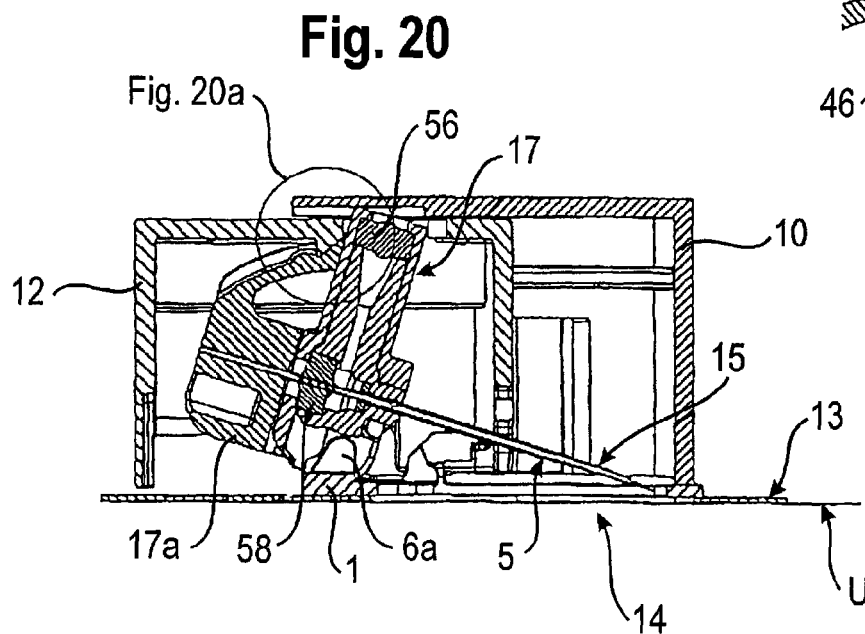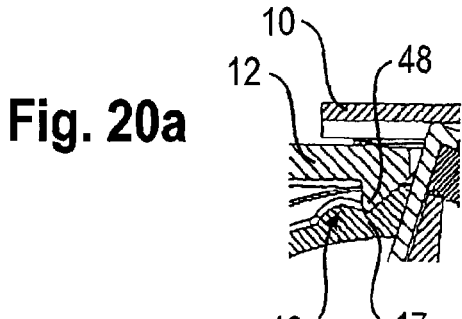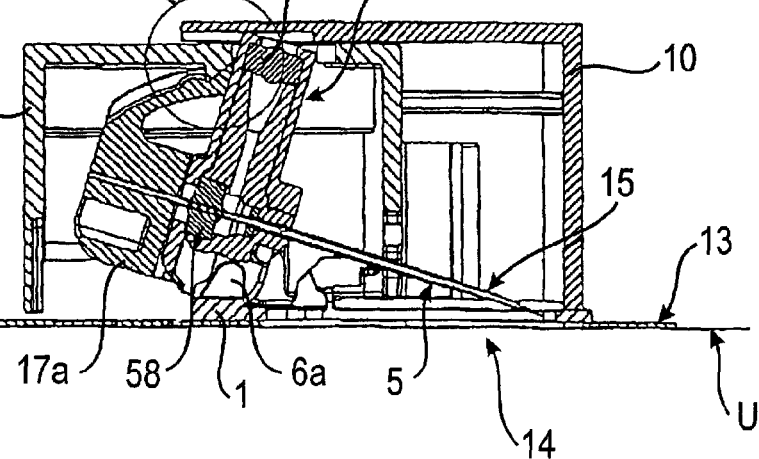

INSERTION HEAD WITH A NEEDLE PROTECTION IN ITS HANDLE

CROSS REFERENCE TO RELATED APPLICATIONS

This application is a continuation of International Patent Application No. PCT/EP2006/005614, filed on Jun. 12, 2006, which claims priority to European Patent Application No. 05 020 157.3, filed on Sep. 15, 2005, the contents of which are hereby incorporated in their entirety by reference therein.

BACKGROUND

The present invention relates to devices for the delivery, administration and passage of medicament and other fluids and methods and uses thereof. The invention relates to an insertion head for medical or pharmaceutical applications, which can be positioned on an organic tissue, such as human skin, and which comprises an insertion means which penetrates into the tissue when the insertion head is positioned on the tissue or after the insertion head has been positioned on the tissue. The insertion head may be part of an infusion set for administering a medicine.

An insertion head is known from DE 198 21 723, comprising a base which comprises a lower side which can be positioned on organic tissue and via which a flexible cannula protrudes which may be immovably coupled to the base and penetrates into the tissue when the base is positioned on the surface of the tissue. For injecting into the tissue, the cannula is stabilized by an injection needle which protrudes through the cannula. In order to protect a user against injuries from the protruding injection needle and to protect the injection needle comprising the insertion means against damage, a cylindrical needle protection is detachably fastened to the lower side of the insertion head. The needle protection requires space, and if carelessly handled, there is a danger of it detaching from the insertion head. The user also requires both hands in order to remove the needle protection, wherein after the needle protection has been removed, one hand is still situated in the immediate vicinity of the then freely protruding injection needle.

German patent application No. 10 2004 039 408.3 discloses an insertion head comprising an insertion means which can be moved from a protective position in which it is accommodated in a receptacle, into an insertion position in which it protrudes beyond the lower side of the insertion head and, when the insertion head is placed on the surface of a tissue, penetrates into the tissue. The receptacle is an integral part of the insertion head which comprises a hollow space which is open towards the lower side. In the protective position, the insertion means may be accommodated in the hollow space such that its free end does not protrude beyond the lower side or laterally. The insertion head does not require a separate protection for the insertion means and is therefore as flat when delivered as it is when being used, i.e. when positioned on the tissue, but is lengthened due to the integrally formed receptacle.

SUMMARY

It is an object of the invention to provide an insertion head which can be safely handled, like for example the insertion head of DE 10 2004 039 408, and is compact when being used, i.e. after it has been positioned on the surface of the tissue and the insertion means has penetrated in.

An insertion head such as the invention relates to comprises a base including a lower side which can be positioned on organic tissue, an insertion means which can be inserted into the tissue, and a receptacle which accommodates at least a free end of the insertion means when the insertion means is in a protective position.

In accordance with the invention, when the insertion means is in the protective position, at least its free end does not protrude beyond the lower side of the base. Rather, the insertion means is movably mounted by the base, such that it can be moved relative to the base from the protective position into an insertion position in which its free end protrudes beyond the lower side. In the protective position, the insertion means may be short of the lower side of the base over its entire length and may be completely or partly shielded and/or hidden from view. In some embodiments, the insertion means in the protective position points parallel or substantially parallel to the lower side or contact area of the base. This favors a flat design for the base, wherein its height is measured at right angles to the lower side. The receptacle may also be detachably coupled to the base, and when coupled, the receptacle may provide protection for the insertion means, such that the base is relieved of this function, and the length on the base which may otherwise be required in order to fulfill the protecting function may therefore be spared. The receptacle is open towards the lower side of the base. An opening for the insertion means may be sufficient, however, in certain implementations, the detachable receptacle surrounds the base or a part of the base in the manner of a cup or dish, such as in the shape of a half-cup or half-dish. The receptacle may be removed upwards from the base once a connection has been released.

To facilitate handling, the insertion head may be fitted with a handle that projects from the base. The handle or at least a handle component may be detachably coupled to the base. Such a handle or handle component may be configured as a detachable receptacle for the insertion means. In another implementation, the handle comprises a handle part, which protrudes from the upper side of the base and from which the receptacle projects laterally.

The handle may have a number of parts including a handle component which can be moved relative to the base and to an additional handle component or a number of additional handle components. The movable handle component may be coupled to the insertion means such that moving this handle component moves the insertion means. An additional handle component, which may form a counter bearing for moving the movable handle component, may be unmoving relative to the base when coupled and may form the detachable receptacle. In principle, the movable handle component may instead form the detachable receptacle. Alternatively, a number of handle components may also jointly form the receptacle.

In certain implementations, the handle may be fitted with a movable handle component, and because of this, the insertion means may be moved by gripping and operating the handle. For example, the handle may provide the counter bearing for the movable handle component. Such a counter bearing is referred to as the additional handle component. The movable handle component may, for example, be a push button. The additional handle component may be a casing from which such a push button protrudes. In certain embodiments, the two handle components jointly form the handle, for example as halves of a two-part handle.

For automatically positioning by means of an inserter in accordance with the invention, the insertion head, according to certain implementations, includes a holding structure, e.g., at its handle, which is in holding engagement with a holding means of the inserter. If the handle includes a handle component immovably coupled to the base, and a handle component which can be moved relative to the handle component, the unmoving handle component may form the holding structure. The holding structure may be moulded on the handle or on the unmoving handle component, for example in one piece, and may be rigidly coupled to the handle or the unmoving handle component.

In some embodiments, the movable handle component may be configured as a receiving member, but is referred to as the movable handle component in the description of the embodiments of the insertion head below. However, in alternative embodiments, the receiving member may not be a handle component but may serve to couple between an activating member and the insertion means.

In further embodiments, the movable handle component may be moved parallel or substantially parallel to the lower side of the base. This may be a linear mobility. As an alternative to a translational mobility, the second component may be attached such that it can pivot.

The at least one additional handle component may be coupled to the base immovably. However, both handle components may be coupled to the base such that they can be moved relative to it.

For transmitting the movement of the movable handle component onto the insertion means, a rigid coupling may be provided, i.e. the movable handle component and the insertion means may be rigidly coupled or moulded in one piece. If, for example, the insertion means can pivot, then a rigid coupling may result if the movable handle component can also be pivoted. As compared to the insertion head of German patent application No. 10 2004 039 408.3, the insertion head in accordance with the invention provides the additional handle component that may serve as a counter bearing for the user, and the force which has to be applied for the pivoting movement does not have to be absorbed by the tissue via the base. Instead, this force may be absorbed by the user holding the additional handle component. Alternatively, if an inserter is used in accordance to the invention to position the insertion head on the tissue and insert the insertion means, the inserter absorbs the force.

In some embodiments, the movable handle component and the insertion means may be coupled via a transmission. In such a coupling, the mobility of the handle component may not correspond to the mobility of the insertion means, but rather the two mobilities may respectively and individually be configured as desired. Thus, the insertion means may be pivoted and the movable handle component may be moved translationally and linearly guided. If the handle component is configured so that it may be pivoted, its pivoting axis may be a different axis to that of the insertion means. While the insertion means may be pivoted about a rotational axis that may be parallel or substantially parallel to the lower side of the base, a pivotable handle component may be pivoted about a rotational axis which is at right angles or substantially at right angles to the lower side. A transmission may, however, also have the rotational axis of a pivotable handle component spaced away in parallel from the rotational axis of the pivotable insertion means. In this case, the pivoting angle of the handle component may be reduced or increased by means of a transmission and transmitted onto the insertion means.

A transmission coupling may comprise a toothed wheel and a toothed rod in a toothed engagement such that the toothed wheel and toothed rod mate with each other when the handle component is moved. The toothed rod may be coupled to the movable handle component such that a movement of the handle component in the longitudinal direction of the toothed rod is transmitted into a rotational movement of the toothed wheel coupled to the insertion means. Given an appropriately fine toothing and/or tooth separation, a comparatively short stroke of the movable handle component may be transmitted into a rotational movement of the toothed wheel, such as a quarter-turn of the toothed wheel. The movable handle component may be configured in one piece with the toothed rod. Instead of a coupling using a toothed engagement via one or a number of pairs of teeth, the coupling may also be configured as a guiding cam and engaging member or may comprise such a guiding cam joint.

As previously discussed, the handle may be detachably coupled to the base according to certain embodiments. Such a coupling may be automatically released when the insertion means is moved into the insertion position when the movable handle component is moved. Alternatively, however, handle or the base may include an additional movable component which, when operated, releases the coupling to the base. The coupling between the handle and the base may be established by a frictional fit, but may also be based on a positive fit or a combination of a positive fit and a frictional fit. In order to create the coupling, the base and the handle may be fitted with at least one connecting element, such that the base and the handle are in engagement when the connection is in place. In order to be able to release the connection, at least one of the connecting elements may be moved out of engagement, against a restoring elasticity force. In certain embodiments, the movable handle component may transfer the insertion means into the insertion position and release the connection by the second handle component moving one of the connecting elements out of engagement against an elasticity force, e.g., by elastically bending the connecting element via a sliding contact. Alternatively, the additional handle component may be configured as a single piece with the base or may be non-detachably fastened to the base. In such an embodiment, however, the additional handle component may be shortened.

If the insertion head does not possess a handle or the detachable receptacle is not part of such a handle, for example by being moulded on the handle in one piece, hand movements required for detaching the receptacle automatically may also move the insertion means from the protective position into the insertion position. Thus, a push button or other operating element may, for example, be attached to the detachable receptacle, or such an element can be suitably coupled to the receptacle, and the receptacle can be detached from the base by operating the operating element.

The insertion means may be a bend-resistant cannula or needle. In some embodiments, the insertion means is flexible, at least in the tissue. The insertion means may exhibit a bending resistance which is reduced when the insertion means is inserted, due to an interaction between the material of the insertion means and the surrounding tissue. Alternatively, the insertion means may also be configured to be flexible, for example as a flexible cannula, and stabilized by a bend-resistant injection means while it is inserted into the tissue. The insertion means may be elongated in an insertion direction and may be slender.

If the insertion means is inherently flexible, it may be stabilized by means of an injection means in order to prevent the insertion means from buckling when it is inserted into the tissue. The injection means may be configured as a thin injection needle. Once the insertion means has been inserted into the tissue, the injection means may be removed. Such an injection means may be removed by removing the detachable receptacle, for example using the handle. If the injection means is not yet coupled to the detachable receptacle in the protective position, it may be coupled automatically to the receptacle, or to a part coupled to the receptacle, as it is moved into the insertion position. For this purpose, a connecting element may be provided on its end facing away from the free end of the insertion means, and the connecting element may pass into a connecting engagement with a connecting counter element coupled to the detachable receptacle, at the same time as the movement into the insertion position is completed or shortly before. The connection or coupling may be a frictional fit, but may also comprise at least a positive fit. The connecting element of the injection means may be configured with a snapping connection with the connecting counter element. Even a hinge with respect to the direction in which the detachable receptacle is to be removed from the base may be sufficient for a positive-fit connection, and accordingly, an elastic snapping engagement may not be required.

In the insertion position, the insertion means may protrude from the lower side of the casing. However, the insertion means may instead also protrude from one side of the casing, providing it protrudes far enough beyond the lower side for penetrating into the tissue. In the insertion position, the insertion means may protrude beyond the lower side of the casing by a length which is adjusted to subcutaneous applications, for example, directly away from or out of the lower side. For applications within the skin or in intramuscular tissue, the insertion means may be correspondingly shorter or longer. It will be understood that the insertion means comprises the longitudinal portion which protrudes into the tissue.

In some embodiments, the insertion means may be permanently and movably coupled to the base. The insertion means may be permanently coupled to the base means such that for the movement from the protective position into the insertion position and/or from the insertion position into the protective position, it is not detached from the base. The insertion means may be permanently coupled to the base in which it cannot be detached from the base at all, or at least not without a degree of exertion of force or not without destroying it.

The insertion means may be coupled to the base such that the insertion means may be pivoted relative to the base. Optionally, the insertion means or at least its free end, once pivoted out, may be pivoted back into the detachable receptacle. In such embodiments, the base and a joint element coupled to the insertion means may provide a rotary joint. The insertion means may project from the joint element simply transverse to the rotational axis of the joint, for example by being moulded onto the joint element, or it may also in principle be coupled to the joint in turn via a joint. In the position which the insertion means is assuming when its free end pivots beyond the lower side, the longitudinal axis of the insertion means and the lower side enclose an acute angle of, for example, less than 50°. The angle may be smaller than 30°, such that at the moment of pivoting out, the longitudinal axis or insertion means points may be substantially parallel to the lower side or contact area of the base. The longitudinal axis of the insertion means, which is pivoted about the rotational axis, may intersect the rotational axis. If the longitudinal axis of the insertion means does not intersect the rotational axis, but rather crosses it at a distance, the distance may be smaller than the length of the insertion means. The distance may be at most half as great as the penetration depth or length of the insertion means. In some embodiments, the pivoting angle of the insertion means is 90°±10°. In other embodiments, however, the pivoting angle may also be smaller if the insertion means in the insertion position does not point at rights angles to the lower side of the base but rather at an acute angle, which however should be at least 30°. Correspondingly, the pivoting angle in such embodiments may be at least about 30° or any intermediate value between about 30° and about 90°. The pivoting angle may also be greater than 90°.

In an alternative embodiment, the base may be arranged as a shifting guide for the insertion means, on which the insertion means is translationally guided as it moves from the protective position into the insertion position and/or from the insertion position into the protective position. In such an embodiment, the base and a joint element which is coupled to the insertion means form a prismatic joint. In certain implementations, the insertion means also simply projects from such a joint element in the shifting direction. In another alternative, the insertion means or an injection means stabilizing it exhibits a bending resistance, which enables the respectively free end of the insertion means or an injection means stabilizing it to bend towards the lower side of the base, into the receptacle, such that the free end protrudes into the receptacle and, in the receptacle, is detachably latched to the base or otherwise detachably held in this bending state against its restoring elasticity. Such an embodiment may be provided when the insertion means in the insertion position and the lower side of the base enclose an acute angle. In order to bend it in this way, the insertion means may be fastened to the base or to the detachable receptacle, slightly short of the lower side of the base, in order to obtain a certain bending line within a hollow space of the insertion head. On the other hand, if the insertion means in the insertion position protrudes directly or as closely as possible from the lower side which contacts the surface of the tissue during use, i.e. is clamped fixedly or such that it can be axially moved and otherwise fixedly—on the lower side or at as short a distance from the lower side as possible, such that a length of the insertion means or of an injection means stabilising it, which can bend when penetrating into the tissue, is as short as possible. An insertion means which in the insertion position projects directly from or close to the lower side may be provided when the insertion means is not bent for the protective position.

Although in some implementations it may be sufficient that the insertion means can be moved in one direction, i.e. once, relative to the base, for example from the protective position into the insertion position, the insertion means may also be moved back and forth between the two positions, such that the insertion means can be moved into the insertion position in order to be used, and back into the protective position in order to be disposed of. For example, the coupling between the insertion means and the casing may comprise a positive fit which may form a joint. Alternatively, the connection may also be a non-positive fit or even a material fit, for example when the insertion means is bent in the protective position.

The insertion head may be a part of an infusion set for administering insulin, an analgesic or some other medicine which can be administered by infusion, or is provided for such a use. Instead of for administering a medicine or any product which can be administered, the insertion head may also serve diagnostic purposes. In such applications, the insertion means may serve as a support for a sensor for measuring for example the glucose concentration in a body fluid or some other physical and/or biochemical parameter which is or can be relevant to a patient's state of health. For diagnostic purposes, the insertion head may also be configured as a perfusion device. In such an embodiment, once the insertion means has been inserted into the tissue, a rinsing fluid flows through it which absorbs one or more constituents of the body fluid as it flows through the tissue, in order to analyze the rinsing fluid enriched with the one or more relevant constituents. Lastly, the insertion head may form a combination of a device for administering a product and a diagnostic means. The insertion means may be appropriately configured for supplying a product, which may be a medicine or a rinsing fluid, or for draining a body fluid or just one or more constituents of a body fluid. In such applications, the insertion means forms at least one flow cross-section. The insertion means may serve to supply and drain substances, also in combination. If the insertion head is configured as a measuring device, then the insertion means may also serve merely to position a sensor or a part of a sensor, i.e. as a mechanical insertion means. In one development as a measuring device, the insertion head may, in addition to mechanically penetrating in, also serve to transmit control signals to the sensor and/or to transmit measurement signals from the sensor. Lastly, in combined applications, it may possess at least one flow cross-section for transporting substances, i.e. a flow conduit, and at least one signal conduit. The signal conduit may be omitted if the sensor is equipped for wirelessly receiving control signals and/or wirelessly transmitting measurement signals. Lastly, the insertion means may also comprise two or more insertion elements which project separately. Thus, a first insertion element may serve to transport substances into the tissue and another, second insertion element can serve to transport substances out of the tissue or merely to penetrate a sensor or a part of a sensor into the tissue. Using a number of insertion portions, which each comprise a flow portion, it may also be possible to administer different substances using the same insertion head. This may also be realized by an insertion means which forms a number of separate flow cross-sections in a common portion.

In accordance with another embodiment, it may be possible to provide a securing link in the receptacle of the insertion head in accordance with the invention, which accommodates the insertion means together with the injection needle or the latter alone in the protective position or in another position such as for instance a locking position, where the insertion means in conjunction with the injection needle, or the injection needle alone can be inserted into the securing link, for example in the protective position in the receptacle. Due to the spring-elastic quality of the injection needle, the tip of the injection needle may be elastically deformed and/or laterally deflected along the securing link into the protective position and/or into the receptacle, when it is pivoted back after use, in order to then latch into a securing cavity behind a securing collar. In this position, the injection needle may then be securely held in the protective position. An injury from the contaminated injection needle may no longer occur.

In accordance with another embodiment, the movable handle component may be shifted far enough into the additional handle component that, once the process for transferring the insertion means from the protective position into the insertion position has been completed, a control ramp on the movable handle component moves against a deflecting ramp on a connecting element which reversibly connects the base to the handle, in order to deflect an engaging element out of its engagement position, such that the handle and the base can be separated. This embodiment, in conjunction with a second path of a link guide, may allow for transferring the insertion head in accordance with the invention from the injection function to the supply function for supplying a medicine, without burdening the patient's tissue.

In accordance with another embodiment, the insertion means may be associated with a holding structure which is moved with the insertion means, where the holding structure comprises a latching collar which, when the additional handle component is drawn out of the movable handle component, enters into a latching engagement with an engaging element, in order to be able to prevent the injection means from pivoting out again.

In accordance with certain embodiments, the receptacle is embodied in one piece with the handle or the additional handle component. In this case, the receptacle may be provided separately from the base.

The insertion means may also be associated with a holding structure which is moved with the insertion means, where the holding structure comprises a securing structure. The latter should oppose a wall of the movable handle component which extends parallel to the movement direction of the movable handle component. This may allow an engaging element on the inner side of the wall to be in reversible engagement with the securing structure when the insertion means is in its protective position. By means of these measures, it may be possible to hold the insertion means in conjunction with the injection needle securely in the protective position in the receptacle, in order to then still be able to pivot the insertion means in conjunction with the injection needle as desired using the movable handle component, once an initial resistance provided by the securing structure and the engaging element has been overcome.

In accordance with another embodiment of the invention, an insertion head may be provided with an insertion means which is held on the base via a rotational or pivoting axis. A link block or trunnion may be provided, which is arranged non-centrically in relation to the rotational axis and in some implementations, separately from it, where a link guide is provided which co-operates with the link block. A movement of the movable handle component relative to the base over a first path of a first portion of the link guide transfers the link block from a first position which corresponds to the protective position of the insertion means or needle, into a second position which corresponds to the insertion position of the insertion means. This embodiment may provide a relatively complex guiding path for the insertion means as it is pivoted out of the receptacle, where at the same time, relatively minor forces have to be exerted via the movable handle component, and jamming between the individual parts of the mechanism is highly unlikely.

In accordance with another embodiment of the invention, a connecting element may be provided which reversibly connects the base to the handle, where in order to detach the handle from the base, the handle may be moved over a second path perpendicular to the extending direction of the insertion means situated in the insertion position, where the link guide comprises a second portion corresponding to the second path, such that when the handle is detached, the insertion means is not moved with it, i.e. by suitably embodying the link guide, it is possible—after the injection needle and the insertion means have been injected into a patient's body—to move the handle parallel to the surface of the body and/or the surface of the flap, also referred to below as the plaster, without straining the organic tissue with parallel forces. In this way, it may be possible to separate the handle region from the base and therefore the injection needle from the insertion means by operating the same component, in this case the movable handle component, in order to perform both triggering and decoupling.

It is therefore possible in accordance with the invention to pivot the contaminated injection means and/or injection needle back into the movable handle component again.

It may also be possible to perform the triggering and decoupling in immediate succession, where the link block already passes the entire link guide, which may alone pivot out the cannula or the insertion means in conjunction with the injection needle, and simultaneously or immediately after decouples the handle components, before the cannula comprising the needle is applied. In this case, a breakable cohesion may remain between the portion remaining in or on the patient's body and the portion of the insertion head, in accordance with the invention, which may be removed.

The insertion means may be associated with a securing structure, which may reversibly restrain the insertion means in the protective position. Thus, for example, the additional handle component may be embodied with a latching collar which may be brought into a reversible engagement with a complementary latching unit on the movable handle component. If a resistance is overcome, the additional handle component may be moved relative to the movable handle component, and the cannula together with the injection needle may be moved or pivoted into the application position.

The insertion means may also be associated with a cannula casing which is moved with the insertion means, where the cannula casing comprises the securing structure. The latter should oppose a wall of the movable handle component which extends parallel to the movement direction of the movable handle component. This may allow an engaging element on the inner side of the wall to be in reversible engagement with the securing structure when the insertion means is in its protective position. By means of these measures, it may be possible to hold the insertion means in conjunction with the injection needle securely in the protective position in the receptacle, in order to then still be able to pivot the insertion means in conjunction with the injection needle as desired using the movable handle component, once an initial resistance provided by the securing structure and the engaging element has been overcome.

In accordance with another embodiment, it may be possible to provide a securing link in the additional handle component of the insertion head in accordance with the invention, which accommodates the insertion means together with the injection needle or the latter alone in the protective position, where the insertion means in conjunction with the injection needle, or the injection needle alone can be latched in the securing link in the protective position in the receptacle. Due to the spring-elastic quality of the insertion means in conjunction with the injection needle, the tip of the injection needle may be elastically deformed and/or laterally deflected along the securing link into the protective position and/or into the receptacle when it is pivoted back, in order to then latch into a securing cavity behind a securing collar. In this position, the injection needle in conjunction with the insertion means may then be securely held in the protective position. The securing link may also be provided in the receptacle or in the movable handle component and/or in portions on different parts.

In accordance with another embodiment, the movable handle component may be shifted far enough into the additional handle component that, once the process for transferring the insertion means from the protective position into the insertion position has been completed, a control ramp on the movable handle component moves against a deflecting ramp on a connecting element, which reversibly couples the base to the handle, in order to deflect a connecting means out of its engagement position, such that the handle and the base can be separated. This embodiment, in conjunction with the second path of the link guide, may allow for transferring the insertion head in accordance with the invention from the injection function to the supply function for supplying a medicine, without burdening the patient's tissue.

The base may be coupled such that it can rotate or pivot to the cannula casing, and the needle holder may be coupled such that it can rotate or pivot to the second or first handle components, where the two rotational and/or pivoting mechanisms exhibit a common center and/or a common axis.

It may therefore be possible, in accordance with the invention, to pivot the contaminated injection means and/or injection needle back into the second handle component again.

BRIEF DESCRIPTION OF DRAWINGS

Example embodiments of the invention are explained below on the basis of figures. Features disclosed by the example embodiments, each individually and in any combination of features, develop the subjects of the claims and also the embodiments described above. There is shown:

FIG. 20 is an insertion head with the insertion means situated in the protective position, in a sectional view;

FIG. 20a is a detail from FIG. 20, also in a sectional representation;

FIG. 21 is the insertion head in accordance with FIG. 20A, with the insertion means situated in the insertion position, also in a sectional representation;

FIG. 23B is an enlarged detail of area C from FIG. 23A

DETAILED DESCRIPTION OF DRAWINGS

Similar or at least functionally similar parts are generally identified below using the same or comparable reference signs, such that in most cases, it has been possible to omit repetition in the description. The parts of the individual embodiments can mostly be exchanged, i.e. combined, with one another. The present invention is more fully described in relation to the figures provided below.

Figure 1:
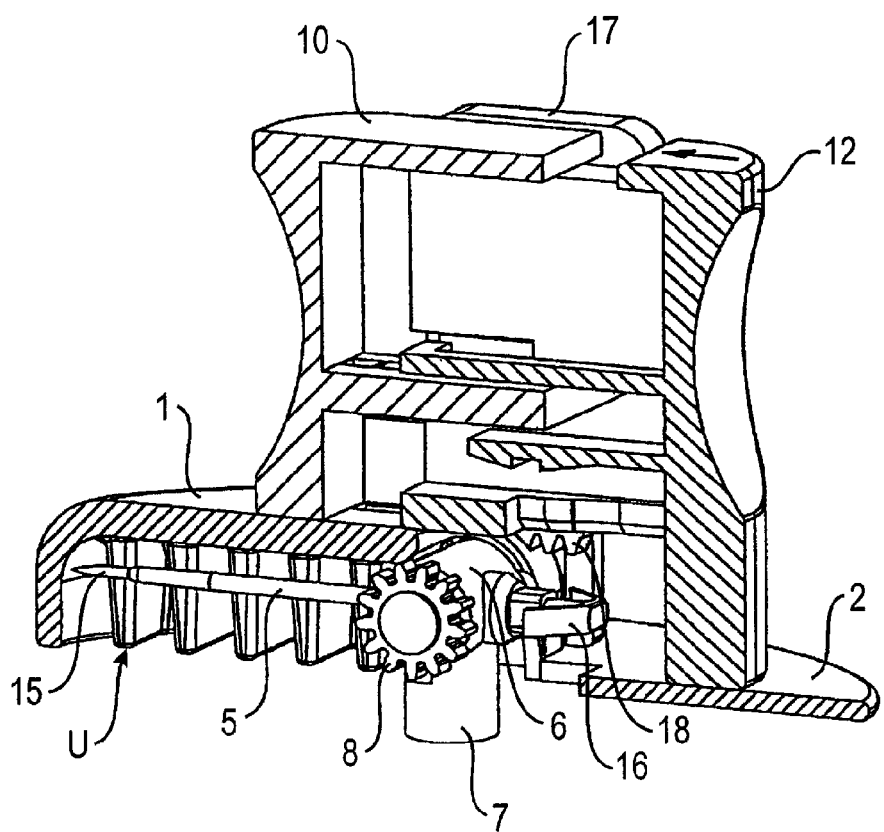
FIG. 1 is an insertion head of a first example embodiment, with the insertion means situated in the protective position.

FIG. 1 shows an insertion head of a first example embodiment, in a longitudinal section. The insertion head comprises a base comprising an accommodating part or receptacle 1 and a flat part 2, which are moulded from plastic in one piece. The lower side U of the base 1, 2 can be positioned on organic tissue. The insertion head also comprises a two-part handle comprising a first handle component 10 and a second handle component 12. The handle component 10 is immovably but detachably coupled to the base. The handle component 12 is movably held on the handle component 10 and the handle component 12 may be linearly shifted both relative to the handle component 10 and relative to the base 1, 2. The axis of mobility of the handle component 12 points parallel to a lower side U of the base 1, 2. The direction of mobility is indicated on the upper side of the handle component 12 by an arrow.

The base 1, 2 mounts an insertion means 5 such that it can pivot about a rotational axis parallel to the lower side U. The insertion means 5 is elongated, and in the example embodiment, it is configured as a flexible cannula. An injection means 15, which protrudes through the insertion means 5, is configured as a thin needle having a sufficient bending resistance to inject the injection means 15, together with the surrounding, conforming or nestling insertion means 5, through the surface of the skin into subcutaneous tissue and so insert the insertion means 5. In certain embodiments, an adhesive pad is attached to the lower side U for fixing the insertion head on the tissue or surface of the skin.

A joint element 6 may be arranged as a shaft of a rotary joint, and with the rotational axis as the joint axis, may provide a pivot for the insertion means 5 and the injection means 15.

The base 1, 2 may be arranged as another joint element of the rotary joint in the form of a socket or also an open bearing eye. On the rotational axis of the joint, an externally toothed wheel 8 is arranged on each of the two sides of the joint element 6 and is non-rotationally coupled to the joint element 6, for example is moulded in one piece. One of the two toothed wheels 8 can be seen in FIG. 1. The other is positioned on the opposite side of the joint element 6 and is hidden by the accommodating part 1 of the base 1, 2. The injection means 15 protrudes through the joint element 6. A supply 7 for a medicinal fluid, for example insulin, is coupled to the joint element 6. The supply 7 projects from the joint element 6, roughly at right angles to the insertion means 5. The joint element 6, together with the supply 7, the toothed wheels 8, the insertion means 5 and the injection means 15, forms a unit in relation to the rotational movement of the joint element 6 and the toothed wheels 8 and the pivoting movement of the other components mentioned.

The movable handle component 12 is provided with two toothed rods 18 which are each in toothed engagement with one of the toothed wheels 8. Of the two toothed rods 18, only the one co-operating with the hidden toothed wheel is depicted in FIG. 1. An identical toothed rod 18 co-operates with the toothed wheel 8 depicted in FIG. 1. If the handle component 12 is shifted in the direction indicated by the directional arrow, during which movement the first handle component 10 guides the handle component 12, the two toothed rods 18 mate with the two toothed wheels 8, such that the shifting movement of the handle component 12 is transmitted into a rotational movement of the joint element 6 and a pivoting movement of the insertion means 5, the injection means 15 and the supply 7.

The pivoting movement transfers the insertion means 5 from its protective position, shown in FIG. 1, into an insertion position. In the protective position, the insertion means 5 and the injection means 15 point parallel or substantially parallel to the lower side U of the base 1, 2. The insertion means 5 and the portion of the injection means 15 protruding in the same direction beyond the joint element 6 may be accommodated in their common protective position in a hollow space enclosed by the accommodating part or receptacle 1, except for the lower side U. Having the insertion means 5 situated in the protective position may reduce the chance of injury on the injection means 15. In addition, the insertion means 5 and the injection means 15 in the protected position may prevent damage due to careless handling. The receptacle 1 may be arranged as a blind, such that the user cannot see the injection means 15 from the upper side of the insertion head, nor from a lateral angle of view. An adhesive pad, which may be attached to the lower side, may be provided with a passage slit for the insertion means 5 and the injection means 15.

The toothed rods 18 are respectively arranged on a lower side, facing the lower side U, of two bend-resistant tongues which protrude in the movement direction from a lateral part of the handle component 12. In addition to the two tongues forming the toothed rods 18, at least one other tongue protrudes in the movement direction from the lateral part of the handle component 12 and serves to linearly guide the movable handle component 12 on a guide provided by the handle component 10.

In order to insert the insertion means 5 into the body tissue below the skin or into the skin, the user grips the handle of the insertion head between his thumb and forefinger. The handle components 10 and 12 are each provided with a correspondingly shaped lateral indentation. By pressing the handle components 10 and 12 together, the movable handle component 12 is pressed up to and against a stopper provided by the first handle component 10. During this movement, the two toothed rods 18 mate with the toothed wheels 8, such that the translational movement of the handle component 12 is transmitted into a rotational movement of the joint element 6 and thus into a pivoting movement of the insertion means 5 and the injection means 15. The path of the handle component 12, the diameter of the toothed wheels 8 and the fineness of the toothings may be chosen such that a movement of the handle component 12 by a few millimeters, for example 4 or 5 mm, generates a pivoting movement of the insertion means 5 and the injection means 15 by a pivoting angle of at or around 90° into an insertion position in which the insertion means 5 and the injection means 15 protrude, at least roughly at right angles, beyond the lower side U of the base 1, 2.

Figure 2:
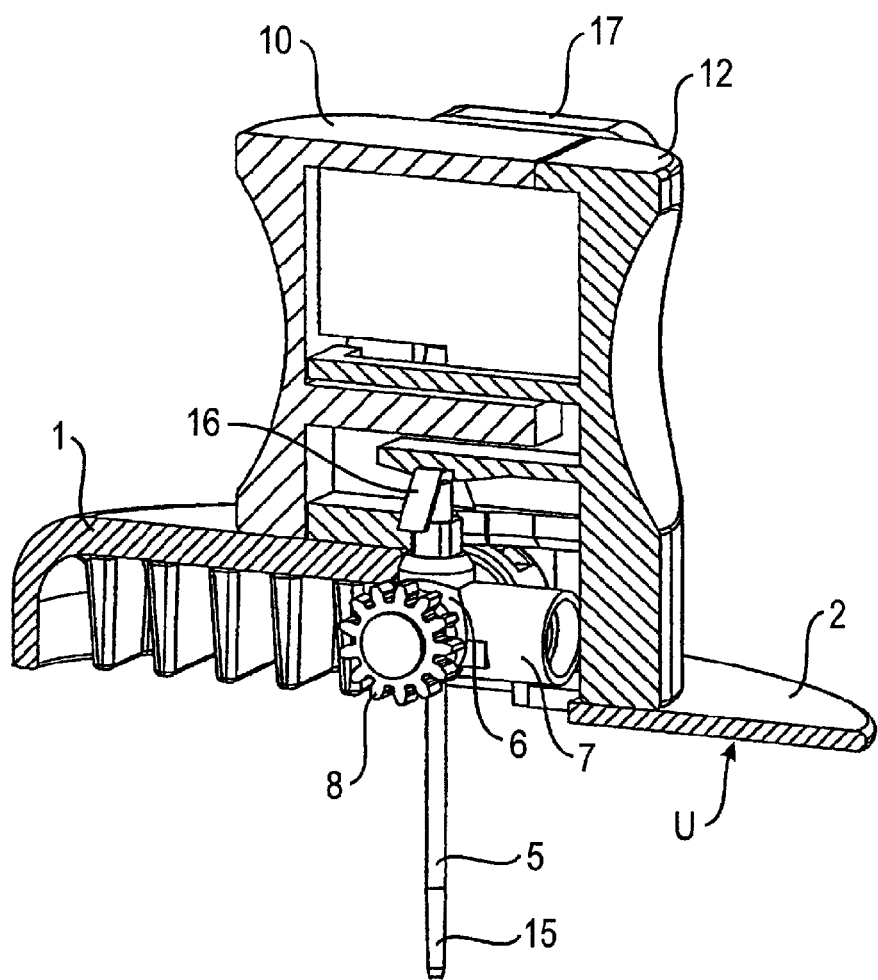
FIG. 2 is the insertion head with the insertion means situated in the insertion position.

FIG. 2 shows the insertion head with the insertion and injection means 5, 15 situated in the insertion position.

At the end of the pivoting movement, the injection means 15 has been coupled to the handle 10, 12, e.g., to the movable handle component 12. In the protective position (FIG. 1), there is no contact between the injection means 15 and the handle 10, 12, such that the injection means 15 can freely pivot together with the insertion means 5. In order to establish the coupling, a connecting element 16 is arranged on, e.g., fastened to, an end of the injection means 15, which is proximal in the insertion position and by which the injection means 15 protrudes beyond the joint element 6. The connecting element 16 comprises one or two protruding fins with which it grips behind a connecting counter element of the handle component 12 in relation to the longitudinal direction of the injection means 15. The connecting counter element of the movable handle component 12 may be configured as a collar area which may grip the connecting element 16.

In order to position the insertion head on the surface of a tissue and insert the insertion means 5 into the tissue, the user holds the insertion head by its handle 10, 12 and moves it towards the surface of the tissue until the injection means 15 penetrates through the surface of the tissue, e.g., human skin, and penetrates into the skin. The conforming or nestling insertion means 5 penetrates along with the injection means 15, until the lower side U of the insertion head is placed on the surface of the tissue and adhesively fixed on the surface of the skin, for example by means of an adhesive pad. In order to administer the medicine, the injection means 15 is removed and the supply 7 is coupled to a medicine reservoir, such as a medicine pump, via a connector which co-operates with the supply 7. In the presently described implementation, handle 10, 12 is detached from the base 1, 2 before the supply 7 is coupled to the base. For example, once handle components 10 and 12 have been pressed or shifted together, the handle components 10, 12 may be detached from the base 1, 2. However, the coupling may be automatically released when the handle component 12 is moved, such that the handle 10, 12 can be drawn off in the proximal direction, e.g., upwards in FIG. 2. During the linear drawing-off movement, the injection means 15 slides through the insertion means 5 and the joint element 6 resulting in the flow cross-section of the insertion means 5 being exposed such that once the injection means 15 has been drawn out, the flow cross-section is also simultaneously fluidly coupled to the supply 7. In this respect, the insertion head can be embodied as described for example in DE 198 21 723 C1 and DE 10 2004 039 408.3, which are herein incorporated by reference in their entireties, for any purpose.

Figure 3:
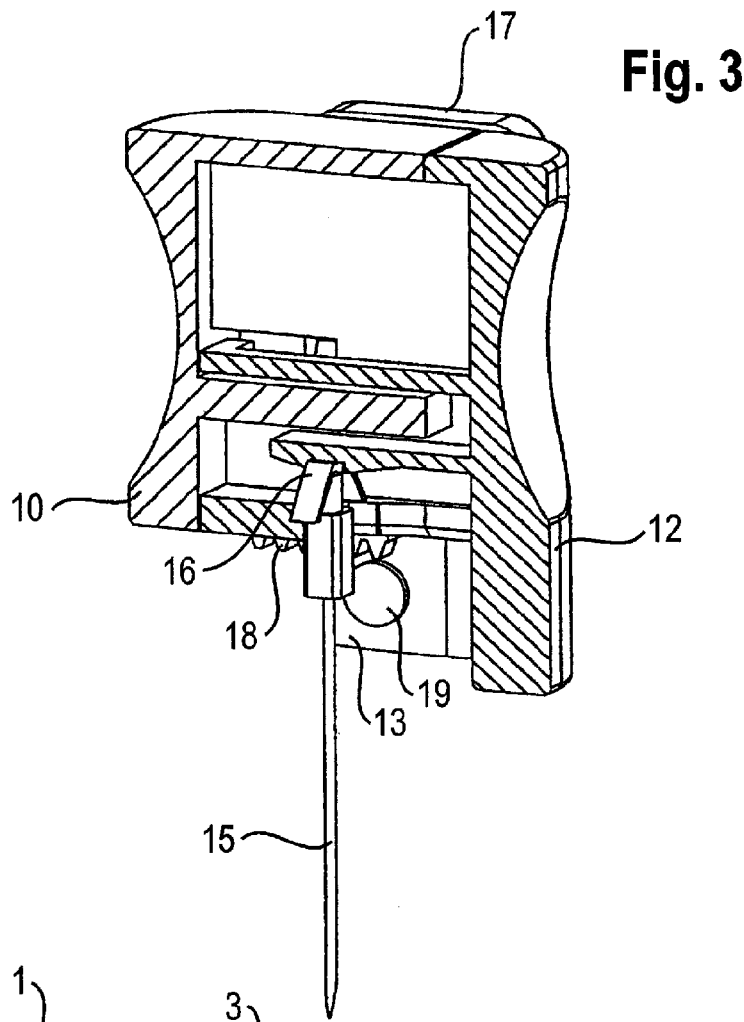
FIG. 3 is a handle of the insertion head of the first example embodiment.
Figure 4:
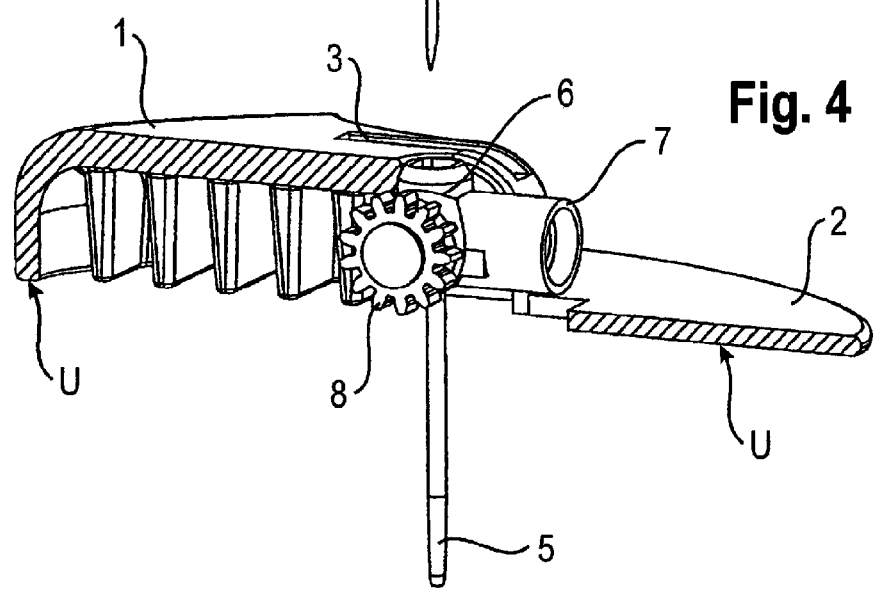
FIG. 4 is a base of the insertion head of the first example embodiment, with the insertion means situated in the insertion position.

FIGS. 3 and 4 show the two parts of the insertion head detached from each other, i.e. the base 1, 2 comprising the insertion means 5 on the one hand, and the handle 10, 12 comprising the injection means 15 on the other hand, in a mutually aligned position in which the longitudinal axis of the insertion means 5 and the longitudinal axis of the injection means 15 are flush with each other. In FIG. 3, a cavity 3 in the base 1, 2 is depicted in which the parts are coupled and the handle component 12 is moved, and one of the two toothed rods 18 retracts into the cavity 3 and mates with the toothed wheel 8 arranged in the cavity 3. The cavity 3 is slit-shaped. A connecting element 19 of the handle 10, 12 is depicted, which when coupled, engages in a positive fit with a connecting counter element of the base 1, 2 and holds the handle 10, 12 on the base 1, 2 and, in combination with contact areas of the handle 10, 12 and the base 1, 2, fixes it relative to the base 1, 2. The connecting element 19 protrudes like a stub from an elastic flap 13 projecting from the handle component 10 in the distal region, in a direction pointing parallel to the lower side U of the base 1, 2 and, when coupled, into a receptacle of the base 1, 2, for example a hole shaped congruently with the connecting element 19, such that a movement of the handle 10, 12 in the longitudinal direction of the injection portion 15 is prevented when the connection exists. In order to release this coupling, another tongue (not shown) which protrudes from the lateral part of the movable handle component 12 moves between the base 1, 2 and the flap 13 bearing the connecting element 19 when the handle component 12 is moved, and bends the flap 13 slightly away from the base 1, 2, but enough to release the positive-fit connection between the connecting element 19 and the connecting counter element, such that the handle 10, 12 comprising the injection means 15 can be drawn off in its longitudinal direction from the base 1, 2.

Figure 5:
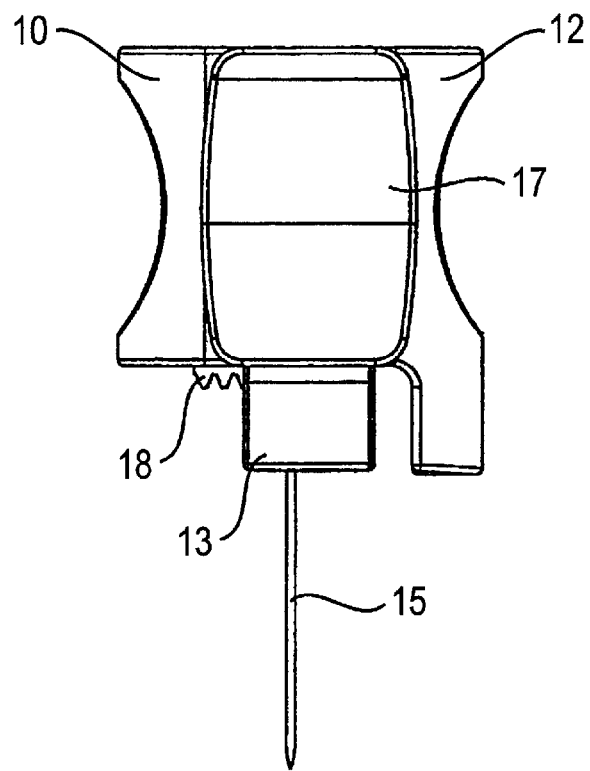
FIG. 5 is the handle of FIG. 3, in a view.

FIGS. 5 and 6 again show the parts of the insertion head detached from each other, in a view onto the rear side facing away in FIGS. 1 to 4. In this view, the connecting counter element 9 of the base 1, 2 depicted in FIG. 6, which when coupled, i.e. in engagement with the connecting element 19, holds the handle 10, 12 on the base 1, 2.

Figure 6:
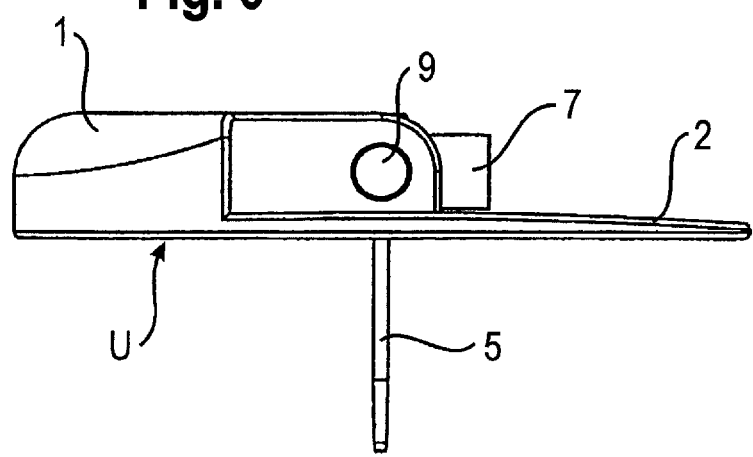
FIG. 6 is the base comprising the insertion means of FIG. 4, in a view.
Figure 7:
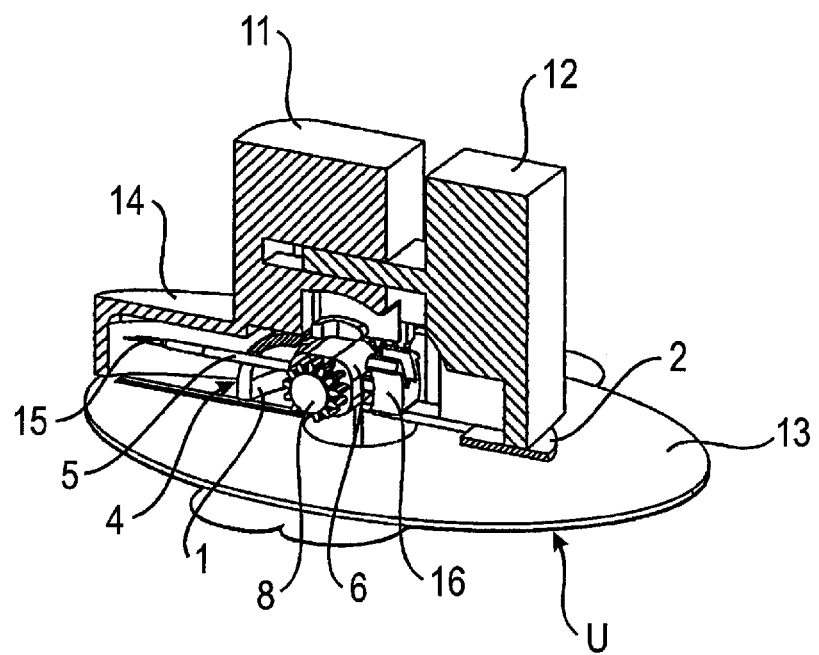
FIG. 7 is an insertion head of a second example embodiment, with the insertion means situated in the protective position.

The base 1, 2 shown individually in FIGS. 4 and 6, which is the support for the insertion means 5 and for the parts 6, 7 and 8 which together with it are configured as a pivoting unit, remains on the surface of the tissue and is in this sense a retained part. By contrast, the handle 10, 12, which then serves as a support for the injection means 15, is disposed of or detached from the injection means 15 again and supplied to another application, while the injection means 15 is disposed of. The retained part 1-9 may be flat and worn under the clothes. The insertion means 5 may be flexible yet stable such that the insertion means is comfortably insertable but stable so that medicine may be reliably supplied.

The handle 10, 12 may also be used in embodiments of the insertion head in which the insertion means is not inherently flexible like the insertion means 5, but is rather bend-resistant enough for injecting without being externally stabilized. In such embodiments, the additional injection means 15 may be omitted. In such embodiments, the handle 10, 12 hands the insertion head and does not support a stabilising injection means 15. An insertion means 5 modified in this way may be configured as an injection cannula having a hollow cross-section or as an injection needle having a solid cross-section and one or more flow channels at its outer circumference, which becomes more flexible after it has been inserted, due to interaction with the tissue.

FIGS. 7 to 10 show a second example embodiment of an insertion head. Aside from the differences described below, the insertion head of the second example embodiment corresponds to the insertion head of the first example embodiment.

Thus, by way of example, an adhesive pad which is fastened to the lower side U is shown, such as could also be attached to the insertion head of the first example embodiment.

The receptacle 1 and the first handle component 11 have been modified as compared to the first example embodiment. Unlike the first example embodiment, the insertion means 5 and the injection means 15 are accommodated in the receptacle 1, which is provided by the accommodating part, over a short portion. In the second example embodiment, the handle component 11 comprises a receptacle 14 for the insertion means 5 and the injection means 15. The receptacle 1 is laterally provided with a cavity 4, in the form of a slit, which is open towards the lower side U and through which the insertion means 5 and the injection means 15 protrude out of the receptacle 1 in the protective position. The receptacle 1 is in turn accommodated in the receptacle 14. The receptacle 14 is open towards the lower side U, but otherwise encloses the insertion means 5 and the injection means 15, for example using an opaque material.

In order to pivot the insertion means 5 and the injection means 15 from the protective position into the insertion position, the user performs the hand movements described in relation to the first example embodiment, i.e. the movable handle component 12 is pressed against the modified handle component 11. When there is a mating toothed engagement, the insertion means 5 and the injection means 15 in the cavity 4 pivot out of the receptacle 1 and receptacle 14, into the insertion position.

Figure 8:
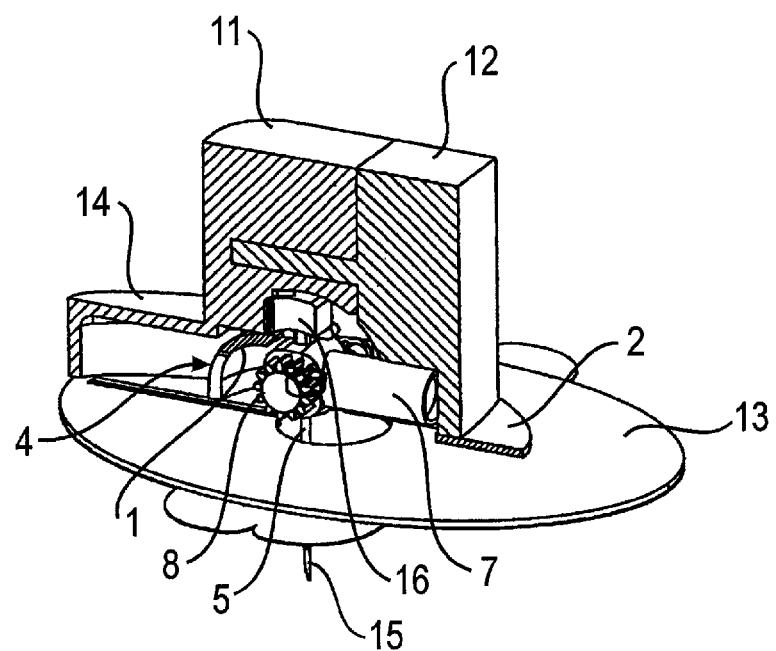
FIG. 8 is the insertion head of the second example embodiment, with the insertion means situated in the insertion position.

FIG. 8 shows the insertion head of the second example embodiment, with the insertion means 5 and the injection means 15 situated in the insertion position.

Figure 9:
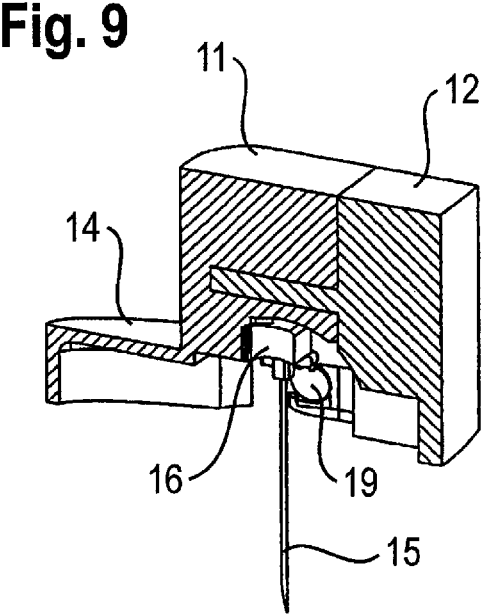
FIG. 9 is a handle of the insertion head of the second example embodiment.
Figure 10:
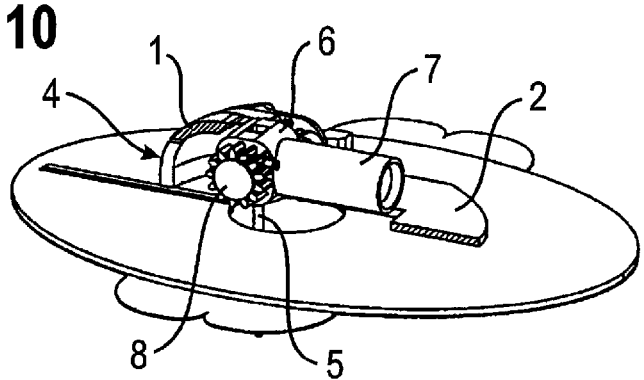
FIG. 10 is a base of the insertion head of the second example embodiment, with the insertion means situated in the insertion position.

FIGS. 9 and 10 correspond to FIGS. 3 and 4 of the first example embodiment. However, as depicted in FIG. 10, the base 1, 2 may be shortened as compared to the base 1, 2 of the first example embodiment, because base 1, 2 does not protect the insertion and injection means 5, 15, but rather the handle 11, 12 serves a protecting function for the insertion means 5 and the injection means 15 in their protective position.

Figure 11:
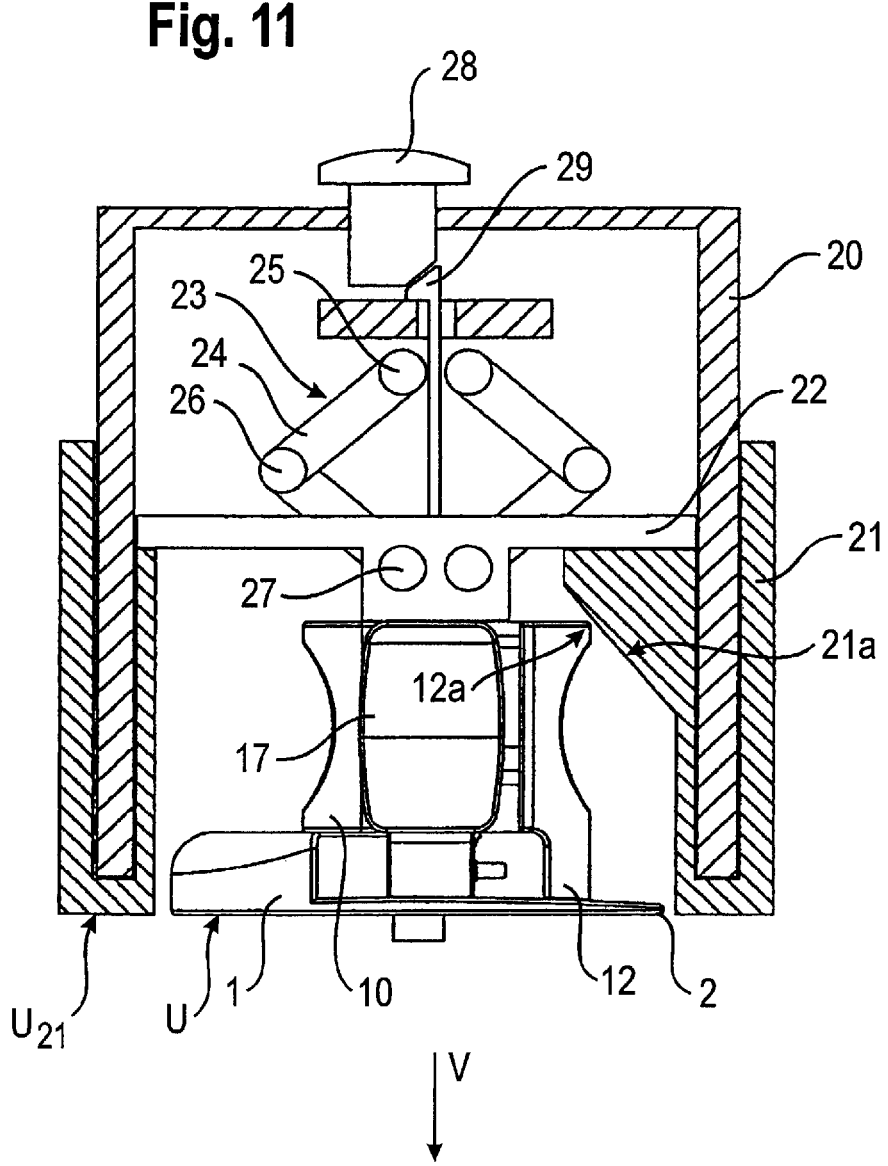
FIG. 11 is a system consisting of an insertion head and an inserter of a first example embodiment, before it has been activated.

FIG. 11 shows a system of a first example embodiment, consisting of the insertion head of the first example embodiment and an inserter, which serves to position the insertion head on the tissue, such that the user does not have to grip the insertion head between his fingers when positioning it. For example, the user does not hold the insertion head by its handle when the insertion means 5 is transferred into the insertion position. This activation of the insertion head is performed with the aid of the inserter. The user may therefore be securely protected against pricking injuries, and the insertion means 5 and the injection means 15 may be securely protected against damage due to careless handling, i.e. by the inserter.

The inserter comprises an inserter casing 20 configured as a sleeve part comprising a base and may exhibit the shape of a cup when viewed from the outside. The inserter casing 20 accommodates a holding means and a drive for the insertion head. The holding means comprises a holding spring, for example a leaf spring, which holds the insertion head in the initial position shown in FIG. 11 relative to the inserter casing 20. In a holding engagement, the holding spring grips behind a holding structure 17, which is arranged on the handle 10, 12 depicted in FIGS. 1, 2, 3 and 5. The holding engagement may be released, against the restoring elasticity force of the holding spring.

The drive comprises an advancing element 22, which may be arranged in the inserter casing 20 such that it is linearly movable in and counter to an advancing direction V. The advancing direction V coincides with a central longitudinal axis of the inserter casing 20. The drive also comprises a force generator 23 which acts on the advancing element 22 in the advancing direction V. The force generator 23 comprises two pairs of legs 24 which may be coupled via a joint, and the two pairs of legs 24 may be arranged symmetrically with respect to the central longitudinal axis of the inserter casing 20, i.e. symmetrically with respect to the advancing direction V. Each of the pairs of legs is suspended in a rotary joint 25 which is fixed relative to the inserter casing 20. The two legs 24 of each pair of legs may be rotatably coupled in a free rotary joint 26. The leg 24 facing away from the fixed joint 25 may also be coupled to the advancing element 22 in a rotary joint 27. One or more springs (not shown) may tense the leg-joint-advancing element arrangement in the advancing direction V. The arrangement of legs 24 and joints 25, 26 and 27 guides the advancing element 22. Additionally or alternatively, the inner surface area of the inserter casing 20 may guide the advancing element 22. A blocking member 29 may also be provided which is in blocking engagement with the inserter casing 20. The blocking engagement may prevent an advancing movement of the advancing element 22. The blocking member 29 may be arranged as the blocking engagement with the cladding structure provided by the inserter casing 20, or equally with another structure which is fixedly coupled to it in relation to the advancing direction V. The blocking engagement may be released by operating a push-button trigger 28.

The inserter also includes an activating member 21 coupled to the inserter casing 20 such that it can move in and counter to the advancing direction V. The activating member 21 may be arranged as a bushing in relation to the inserter casing 20, such that a two-part telescoping inserter casing comprising casing parts 20 and 21 is obtained. For the sake of distinguishing it with regard to its function, however, the casing part 21 shall continue to be referred to as the activating member. The activating member 21 forms the lower side $U_{21}$ of the inserter, via which the inserter may be placed on the surface of the tissue in order to position the insertion head. In the initial position of the insertion head in FIG. 11, the lower side $U_{21}$ of the inserter and the lower side U of the held insertion head each point in the advancing direction V, which may form a surface, e.g., substantially normal surface, for the two lower sides.

The activating member 21 comprises an outer sleeve part and an inner sleeve part which may be coupled on the lower side $U_{21}$ and leave an annular gap. The inserter casing 20 protrudes into the annular gap and guides the activating member 21 in a sliding movement.

In the state shown in FIG. 11, the activating member 21 assumes a retracted position relative to the inserter casing 20, and the inserter exhibits its shortest length as measured in the advancing direction V. In this state of the inserter, the insertion head is inserted, i.e. brought into holding engagement with the holding means of the inserter. Instead of inserting the insertion head, the inserter may also be placed over the insertion head lying on a support. The position and geometry of the holding means may be chosen such that the holding engagement is automatically established when the inserter is placed on the insertion head. Immediately after the insertion head has been accommodated, for example by being inserted, the insertion means 5 of the insertion head is situated in its protective position. In this sense, the insertion head may be inactive. The inserter includes means, i.e. the activating member 21, which when operated can move the insertion means into the insertion position and so activate the insertion head.

In order to activate the insertion head, the activating member 21 and the insertion head together form a joint, e.g., a cam joint. The two joint elements of the joint are a guiding cam 21a, which forms the activating member 21, and an engaging element 12a provided by the movable handle component 12. In the coupling via which the activating member 21 acts on the insertion means 5, the movable handle component 12 may provide an input and/or receiving member of the insertion head. If the activating member 21 is moved in the advancing direction V relative to the inserter casing 20, the guiding cam 21a slides over the engaging element 12a, i.e. over the contact area of the receiving member such as the movable handle component 12, which forms the engaging element 12a. Due to the pressing contact and the profile of the guiding cam 21a which is inclined with respect to the advancing direction V, the handle component 12 is moved transverse to the advancing direction V, towards the additional handle component 10, and the insertion means 5 pivots into the insertion position, as described for the insertion head itself. The movable handle component 12 forms the engaging element 12a at its upper end facing away from the base 1, 2, e.g., with its outer edge. The guiding cam 21a faces the lower side $U_{21}$ of the inserter. The inclination is chosen such that the guiding cam 21a is inclined, from an end facing away from the lower side $U_{21}$, in the advancing direction V away from the insertion head and/or the insertion means 5 which is pivoted out when activated or from the central longitudinal axis of the inserter. The angle of inclination may be constant throughout such that the guiding cam 21a is a slant, i.e. an oblique line or area.

For practical handling, it may be suitable for the user to hold the inserter by the activating member 21 with one hand after the insertion head has been accommodated, for example by gripping around the activating member 21, and to draw the inserter casing 20 counter to the advancing direction V relative to the held activating member 21 with the other hand. This is also understood to mean operating the activating member. The advancing element 22 and the force generator 23 may be moved together with the inserter casing 20 relative to the activating member 21. The insertion head held in the initial position may be slaved by the holding means, i.e. it may be moved relative to the activating member 21, counter to the advancing direction V. The engaging element 12a slides along the guiding cam 21a. Via this interface which is based on a pressing contact, the movable handle component 12 is moved transverse to the advancing direction V, and the insertion means 5 pivots into the insertion position. The insertion head may be activated at the end of the extending movement which the inserter casing 20 and the activating member 21 perform relative to each other.

Figure 12:
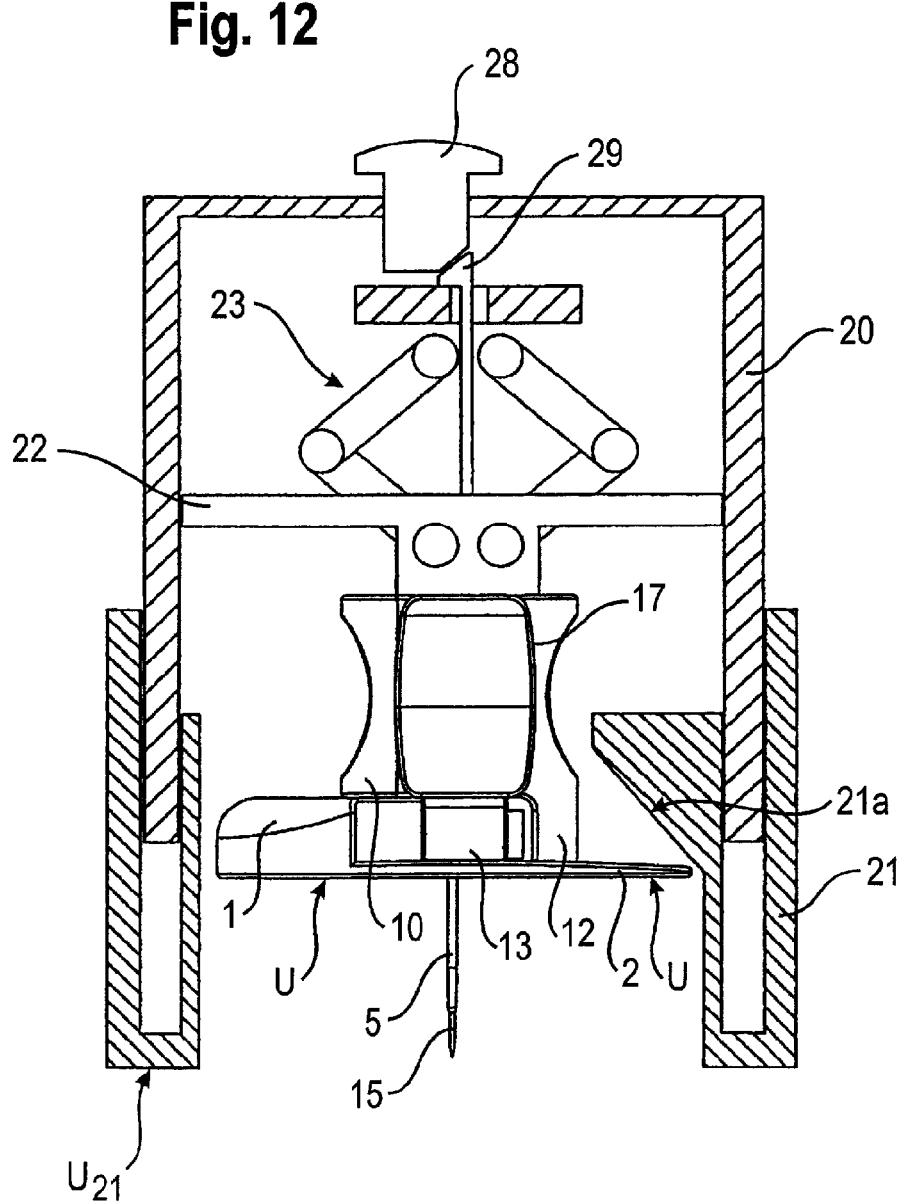
FIG. 12 is the system of the first example embodiment, after it has been activated.

FIG. 12 shows the system consisting of the inserter and the insertion head in its activated state. The inserter casing 20 and the activating member 21 assume their extended position relative to each other. In the extended state, the walls of the inserter casing 20 and the activating member 21 surround the activated insertion head up to and beyond the free end of the insertion means 5 and the injection means 15, i.e. the tip of the injection means 15 is slightly short of the lower side $U_{21}$ of the inserter.

In the extended position, the inserter casing 20 and the activating member 21 are blocked relative to each other. Relative movements in or counter to the advancing direction V are not possible in the blocked state. Upon reaching the extended position, the inserter casing 20 and the activating member 21 may be automatically blocked on each other.

In order to position the insertion head, a user may place the inserter on the surface of the skin. When the inserter has been placed, the user presses the trigger 28. The trigger 28 acts on the blocking member 29 via a cam joint, for example, via a pair of slants. Due to the action of the trigger 28, the blocking member 29 may be moved out of its blocking engagement with the inserter casing 20, such that the advancing element 22 can be moved in the advancing direction V due to the action of the force generator 23. The force generator 23 may abruptly accelerate the advancing element 22, and the advancing element 22 may act on the insertion head like a hammer. In the first portion of the advancing movement, the holding spring springs out of its holding engagement with the holding structure 17 of the insertion head, i.e. the holding engagement is released. The acceleration of the advancing element 22 in the advancing direction V may be large enough for the pressing contact between the advancing element 22 and the insertion head to be securely maintained, at least until the lower side U of the insertion head is at the same height as the lower side $U_{21}$ of the inserter and is thus positioned on the surface of the tissue. According to certain implementations, the injection means 15 and insertion means 5 may have penetrated through the surface of the skin and into the tissue.

After the insertion head has been positioned on the surface of the skin, the user grips the handle 10, 12 and draws it off from the base 1, 2, where the injection means 15 may be automatically drawn out of the insertion means 5 and off from the base 1, 2.

In order for the injection means 15 to also be drawn out automatically, the holding engagement between the holding means of the inserter and the holding structure 17 of the insertion head may be maintained by a modification to the inserter and may not be released by the acceleration of the advancing element 22, as in the example embodiment described. In such a modification, the holding means may be coupled fixedly to the advancing element 22, such that it is slaved in its discharge movement in the advancing direction V. In order to release the holding engagement, the inserter may be fitted with a deflector which, after the inserter has been removed from the tissue and when the inserter casing 20 and the activating member 21 are shifted together, automatically releases the insertion head from the holding engagement. Alternatively, such a deflector may also be provided independently of the activating member 21, and may be separately operated in order to release the holding engagement.

Figure 13:
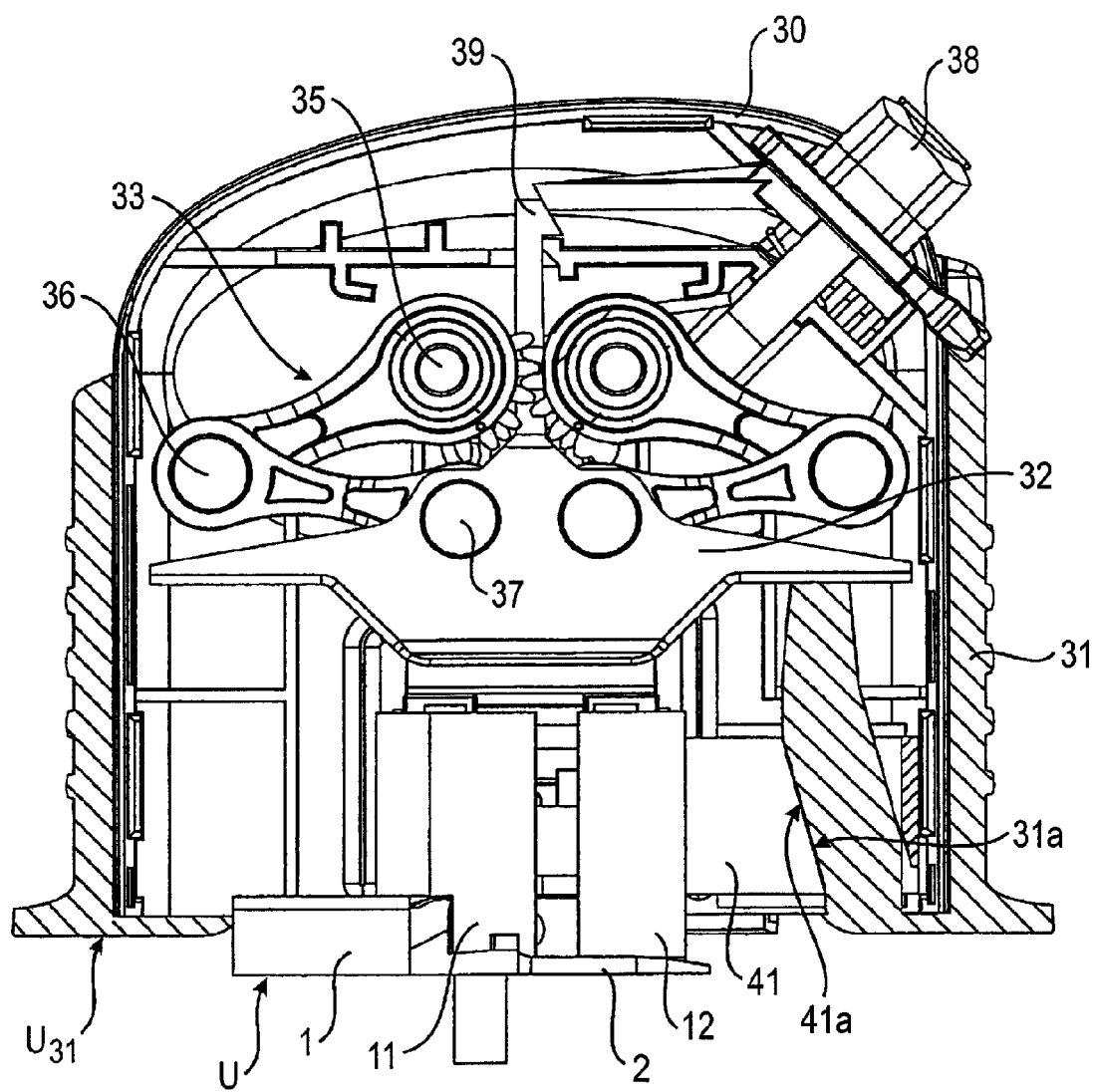
FIG. 13 is a system consisting of an insertion head and an inserter of a second example embodiment, before the insertion head has been activated.
Figure 14:
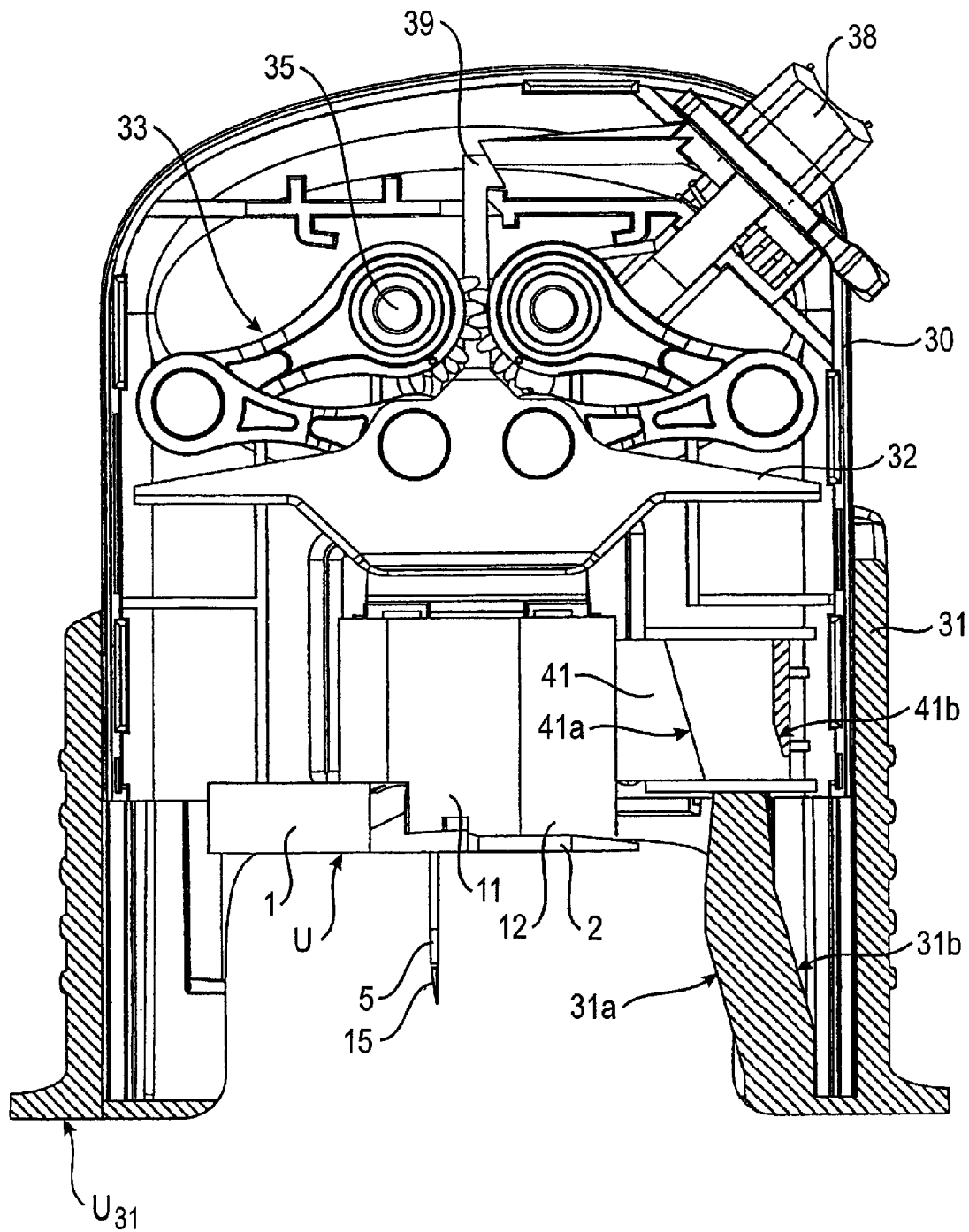
FIG. 14 is the system of the second example embodiment, after it has been activated.
Figure 15:
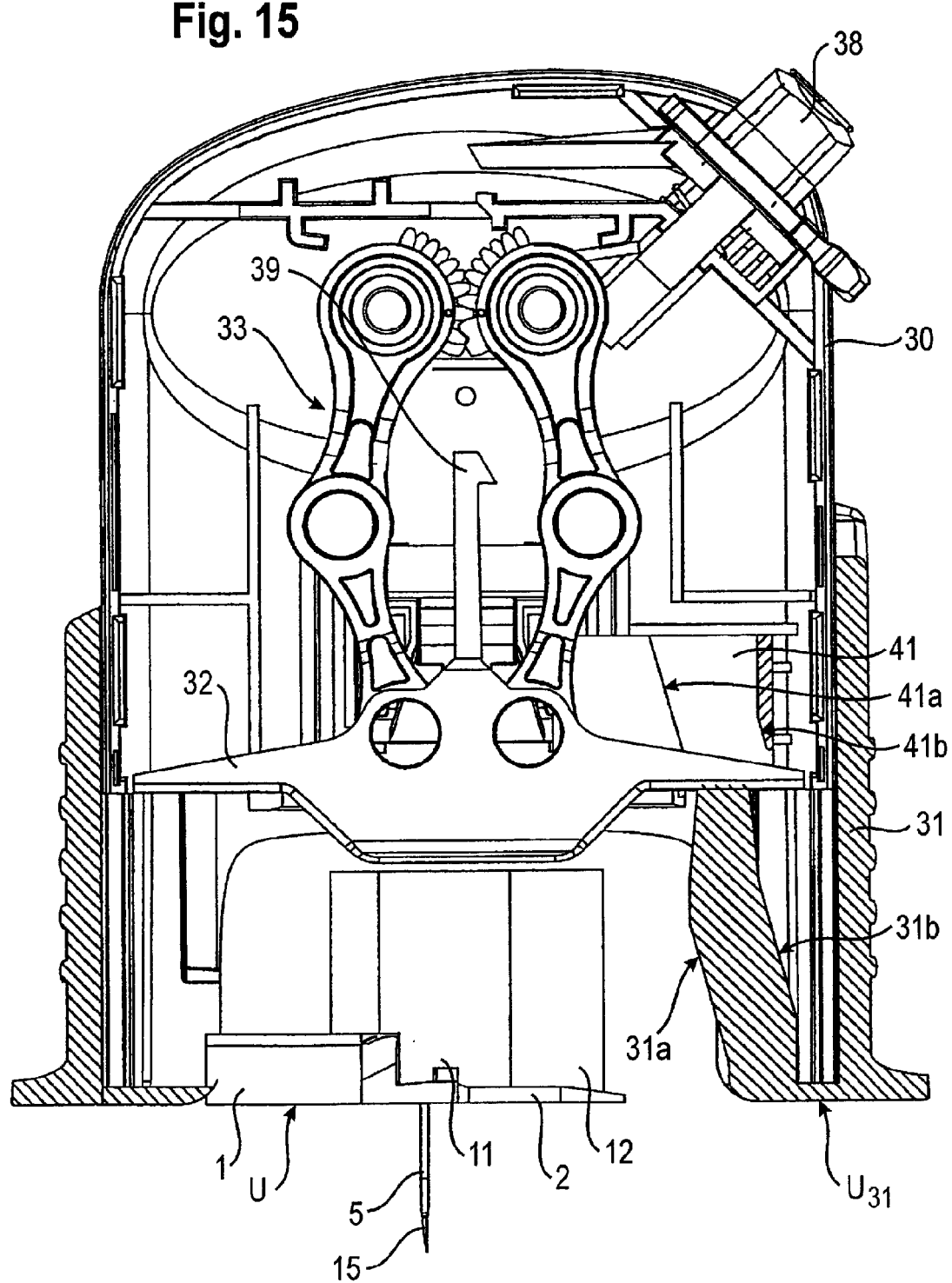
FIG. 15 is the system of the second example embodiment, after the insertion head has been positioned on the surface of a tissue.

FIGS. 13-15 show a system of a second example embodiment, consisting of an insertion head and an inserter. The insertion head may be any of the insertion heads provided in the example embodiments, or combinations or variants thereof. According to the embodiment of FIGS. 13-15, the inserter is modified. The components of the inserter of the second example embodiment which in relation to their function are comparable to the components of the inserter of the first example embodiment are respectively marked with the reference signs of the first example embodiment, raised by the number 10. Thus, the statements made with respect to the first example embodiment may apply to the inserter casing 30 and the activating member 31, as far as their shape and connection and also their relative mobility are concerned. The same also applies in relation to advancing element 32, the holding means and the force generator 33, and also the trigger 38 and the blocking member 39. Where no reference is made in the following to differences, and nothing contrary is shown by the figures, the statements made with respect to the first example embodiment likewise also apply to the second example embodiment.

The inserter of the second example embodiment differs from the inserter of the first example embodiment with regard to the joint via which the activating member 31 acts on the insertion head, in order to activate it through the drawing-up movement of the inserter casing 30 relative to the activating member 31. In the second example embodiment, the inserter itself provides the joint, i.e. comprising two joint elements 31a and 41a, one of which forms the activating member 31 and the other of which forms an effector member 41. The effector member 41 may be mounted by the inserter casing 30 such that it is movable back and forth transverse to the advancing direction V, e.g., at right angles to the advancing direction V. The joint 31a, 41a may be a cam joint. The guiding cam 31a may correspond to the guiding cam 21a of the first example embodiment. The effector member 41 provides the engaging element 41a which slides along the guiding cam 31a when the inserter is lengthened and, due to the inclined profile of the guiding cam 31a, generates a transverse movement of the effector member 41 towards the central longitudinal axis of the inserter when the inserter is drawn up. The movement pointing counter to the advancing direction V, which the inserter casing 30 performs relative to the activating member 31 when it is drawn up, is thus converted in the joint 31a, 41a into the transverse movement of the effector member 41. Its joint element or engaging element 41a may be configured like a guiding cam, but in terms of transmission may be referred to here as the engaging element. The engaging element 41a may alternatively, for example, also be shaped as a cam or burl. The engaging element 41a may equally be referred to as a guiding cam, and in another modification, the joint element 31a may be configured as a protruding cam or burl.

The interface via which the inserter activates the insertion head may be configured as a pressing contact and exists between the effector member 41 and the receiving member or movable handle component 12 of the insertion head. This pressing contact, e.g., loosely pressing contact, may simplify handling because a joint connection may not need to be established in order to the activate the insertion head. For example, it may be sufficient to accommodate the insertion head in combination with operating the activating member 31, which, in the example embodiments may be performed by the drawing-up movement. The pressing contact, i.e. the pressing force exerted by the effector member 41, acts on the movable handle component 12 parallel to the direction of its mobility relative to the base 1, 2. By interposing the effector member 41 and moving the joint 31a, 41a completely to the inserter, there may be in the second example embodiment no force exerted on the handle component 12 transverse to the direction of mobility of the handle component 12.

FIG. 14 shows the system with the insertion head activated. In the course of the drawing-up movement of the inserter casing 30, which is also understood to mean operating the activating member 31, the insertion means 5 and the injection means 15 have been pivoted into the insertion position, such that their common longitudinal axis points in the advancing direction V. The movable handle component 12 has released the coupling between the handle 10, 12 and the base 1, 2, as described for the insertion head. However, the frictional fit between the insertion means 5 and the injection means 15 holds the base 1, 2 on the handle 10, 12 in the holding engagement, as in the first example embodiment.

The blocking engagement, in which the blocking member 39 is still situated with the inserter casing 30 or a structure fixedly coupled to the inserter casing 30, may be released by operating the trigger 38, and the force generator 33 accelerates the advancing element 32 in the advancing direction V. The acceleration may be abrupt, such that the drive means 32, 33 of the second example embodiment also acts like a hammer. The drive force may be generated by two leg springs, each one of which acts on one of the two pairs of legs. The legs 24 which are fastened via the rotary joints 35 (fixed), 36 and 37 and are coupled via a toothed engagement which may provide a synchronous extending movement of the two pairs of legs.

In order to prepare the inserter for another application, after the insertion head has been positioned, the effector member 41 id moved from the position shown in FIG. 14 back again into the position shown in FIG. 13. For this return movement, the activating member 31 and the effector member 41 form an additional joint 31b, 41b, which in the example embodiment is a cam joint. The activating member 31 forms the guiding cam 31b for the additional joint, and the effector member 41 forms the engaging element 41b. The guiding cam 31b may run parallel or substantially parallel to the guiding cam 31a. The guiding cams 31a and 31b may be provided on the inner sleeve part of the activating member 31 such that the guiding cam 31a is arranged at the inner area and the guiding cam 31b is arranged at the outer area of the inner sleeve part. The guiding cams 31a, 31b may oppose each other at roughly the same height in terms of the advancing direction V. The engaging element 41b may also oppose the engaging element 41a at a distance, such that the inner sleeve part of the activating member 31 may retract and extend between the two engaging elements 41a and 41b.

FIG. 15 shows the system of the second example embodiment with the insertion head positioned. The inserter is removed from the insertion head. The user may then draw the handle 10, 12 off from the base 1, 2 and couples the insertion head to a catheter of an infusion pump. Alternatively, the holding means may be coupled fixedly to the advancing element 32 and may hold the handle 10, 12, and the inserter with the handle 10, 12 may be removed from the base. The holding engagement may be released, for example by means of an additional deflector, and the handle 10, 12 may disposed of, with the injection means 10 or on its own.

In order to prepare the inserter for use with another insertion head, the user shifts the inserter casing 30 and the activating member 31 back together into the retracted position, as shown in FIG. 13 with the insertion head retracted. During the retracting movement, the inner sleeve part of the activating member 31 moves between the engaging elements 41a and 41b of the effector member 41. During this retracting movement, the additional joint coupling between the guiding cam 31b and the engaging element 41b may be established. During the retracting movement, the effector member 41 may thus be moved in the joint 31b, 41b, into the end position assumed in FIG. 13, i.e. is moved transversely, e.g., radially, outwards in relation to the central longitudinal axis of the inserter.

The advancing element 32, which is extended due to the action of the spring means 33 in the advancing direction V, opposes an end-facing side of the inner sleeve part facing away from the lower side $U_{31}$ of the activating member 31. The advancing movement of the advancing element 32 may be stopped by an abutting contact against this end-facing side. The activating member 31 is geometrically dimensioned such that when the telescope 30, 31 is in the extended position, the activating member 31 stops the advancing element 32 exactly when the lower side U of the insertion head has reached the height of the lower side $U_{31}$ and therefore just contacts the surface of the skin when the inserter is placed on the skin. During the retracting movement of the inserter casing 30 relative to the activating member 31 or of the activating member 31 relative to the inserter casing 30, the advancing element 32 may be pressed deeper into the inserter casing 30, against the force of the force generator 33, due to the abutting contact by the activating member 31, until the blocking member 39 is in blocking engagement again, as shown by way of example in FIGS. 13 and 14.

Figure 16:
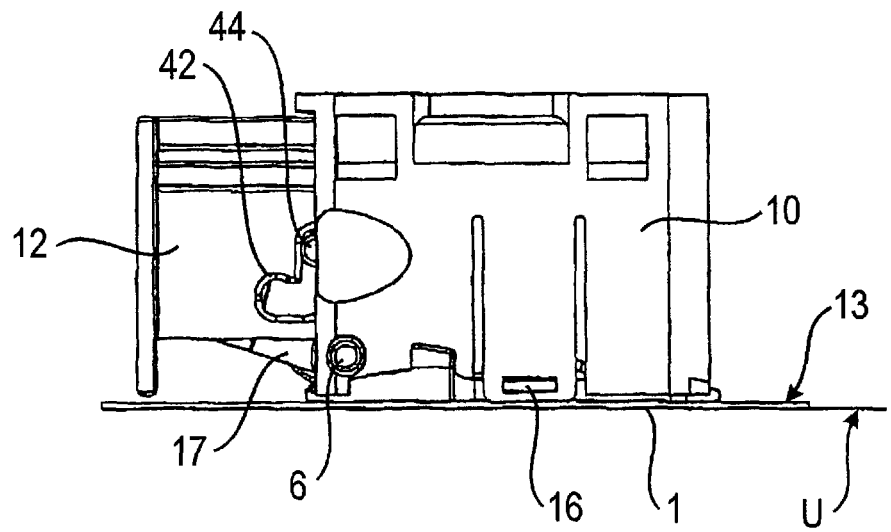
FIG. 16 is an insertion head with the insertion means situated in the protective position, in a lateral view.

FIG. 16 shows another embodiment of the insertion head in accordance with the invention. The insertion head comprises a movable handle component 12 which may be shifted into an additional handle component 10. Shifting the movable handle component 12 into the additional handle component 10 pivots a cannula casing 17b about a joint 6, where the cannula casing 17b still bears the insertion means 5 and the injection means 15 in the protective position. While the movable handle component 12 is operated, the link block 44 in the link guide 42 may be moved downwards towards the joint element 6, which causes a rotational or pivoting movement for the holding structure 17 and therefore for the insertion means and the insertion needle. As soon as the link block or trunnion 44, e.g., with a cylindrical projection on one or both sides, has entered the cam region of the link guide 42, the pivoting movement from the protective position into the insertion position has been completed. The additional handle component 10 is also fitted with a connecting means 16b which is in engagement with a corresponding portion 49 on the base 1, so as to reversibly connect the base to the handle 10, 12.

The link block 44 can of course also exhibit a different position.

Thus, the link block 44 may also be arranged further down and then travel upwards when the parts 17a, 17b are pivoted. Different configurations for the link guide and the link block are possible here.

Figure 17:
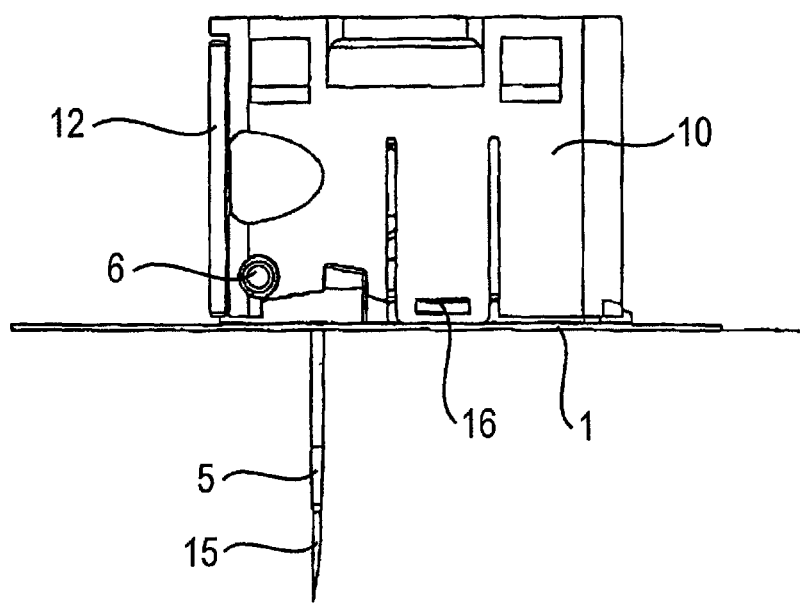
FIG. 17 is the insertion head according to FIG. 16, with the insertion means situated in the insertion position.

In FIG. 17, the movable handle component 12 is sunk into the additional handle component 10, where the insertion movement of the movable handle component 12 into the additional handle component 10 has caused the insertion means 5, together with the injection means 15, to be pivoted out of the receptacle 14 (see FIG. 19) into the insertion position. This embodiment in accordance with FIGS. 16-19 therefore provides a coupling between the handle components and the pivotable insertion means which is an alternative coupling to the embodiments discussed above.

Figure 18:
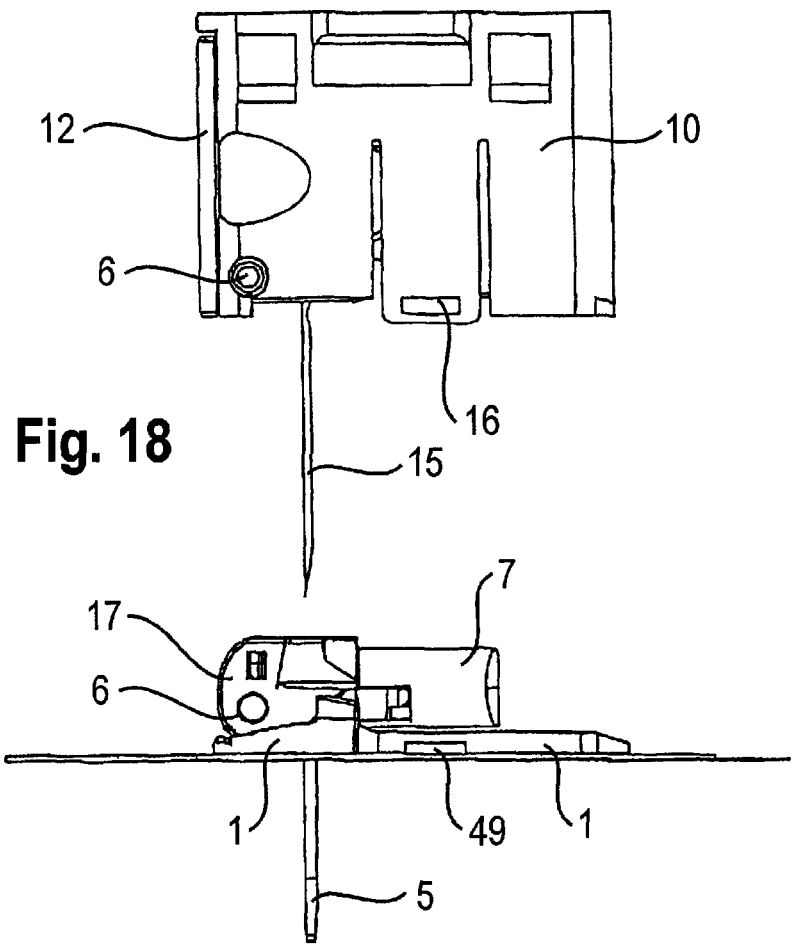
FIG. 18 is the insertion head according to FIGS. 16 and 17, where the handle together with the injection needle is separate from the base together with the insertion means.

FIG. 18 shows how the handle, consisting of the handle components 12 and 10, can be decoupled from the base 1. The base 1 contains a cavity 49 with which a connecting means 16b on the handle 10, 12 was in engagement (see FIGS. 16 and 17), whereas in the representation in accordance with FIG. 18, this engagement has been broken, such that the handle 10, 12 can be drawn off from the base 1.

Figure 19:
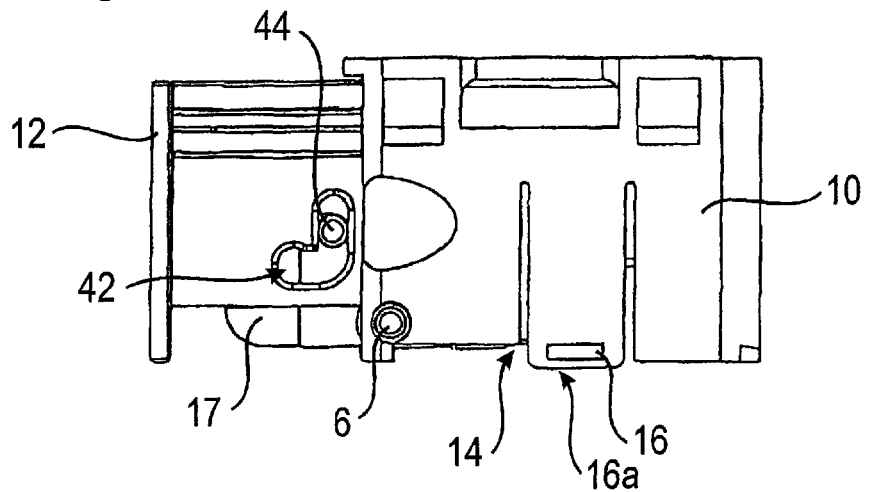
FIG. 19 is the additional handle component and the movable handle component, detached from the base, in a lateral view.

FIG. 19 shows the handle 10, 12 in accordance with FIG. 18, where the movable handle component 12 is drawn out of the additional handle component 10, such that the link block or trunnion 44 in the link guide 42 has been guided upwards, whereby the cannula casing 17b and the needle holder 17a with the injection means 15 fixed to it have again been pivoted into the original protective position in the receptacle 14 or a locking position close to it. The connecting means 16b, which is positioned at the end of a spring stay 16a, then has no function, since it no longer has to hold a connection to the base 1.

FIG. 20 shows the insertion head in accordance with another embodiment in accordance with the invention, in a situation before an application and/or during storage. The insertion means 5 with the injection means 15 partially accommodated in it is situated in the protective position in the receptacle 14. On the flap 13 or plaster 13, a protective film is applied to the lower side, in order to actively hold the adhesion points of the plaster 13. A septum 58 is also provided such that the injection means 15 may be inserted and removed. In addition, septum 58 provides a seal for the insertion means 5. The connection portion coupled perpendicularly to the injection means 15 may correspondingly also be provided with a septum 56 which is intended to enable a sealed connection to a supply conduit or connector (see FIG. 28).

On a needle holder 17a which is arranged on the cannula casing 17b and holds the injection means 15, a securing structure 46 is provided on the side facing away from the base 1, as shown by the image detail in accordance with FIG. 20a. In the state shown, an engaging element 48 is in engagement with the securing structure 46 and provides a resistance which acts against the movable handle component 12 being inserted into the additional handle component 10 by accident. The operator of the insertion head in accordance with the invention in accordance with this embodiment has to initially apply an increased force, in order to overcome the engagement between the engaging element 48 and the securing structure 46, so as to perform the pivoting process for the insertion means 5 together with the injection means 15 from the protective position in the receptacle 14 as shown in FIG. 20a, into the application position as shown in FIG. 21.

It is also possible to realize the securing structure 46 using latching means corresponding to the elements 52, 54, which can for example be provided on the additional handle component 10 and the movable handle component 12 and unlatched by shifting one into the other.

Figure 22:
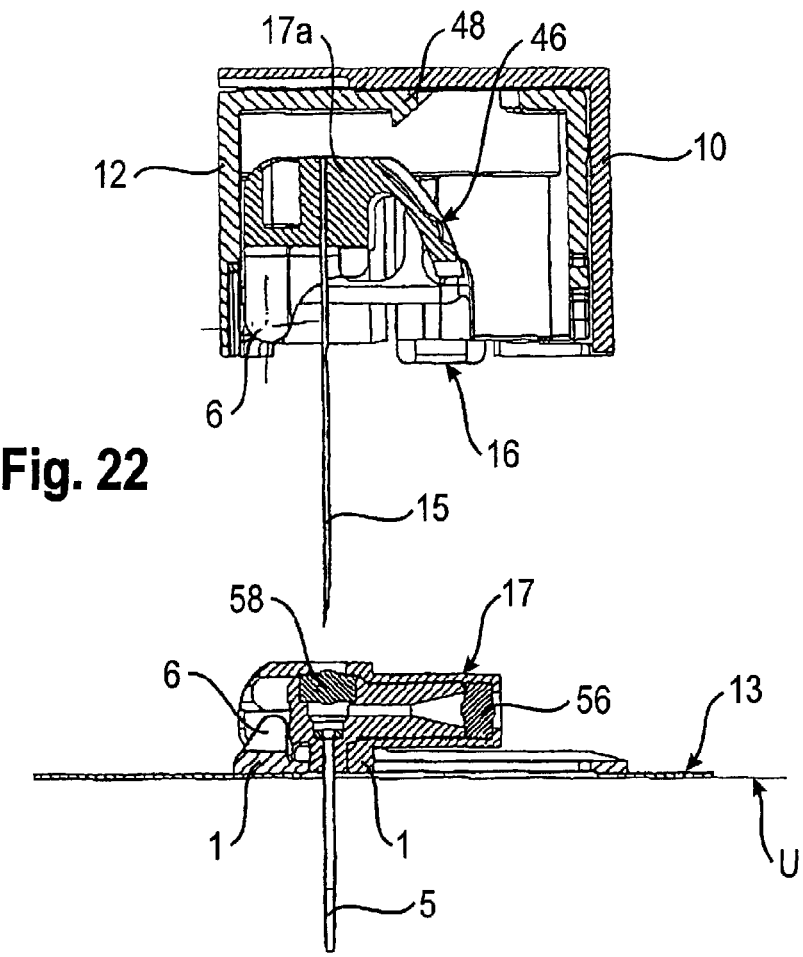
FIG. 22 is a sectional representation of the handle together with an injection portion, separate from the base comprising the insertion means which can be positioned on the patient.

The insertion means 5 together with the injection means 15, which are injected into a patient's tissue in FIG. 21, are disassembled in accordance with FIG. 22, i.e. the injection means or injection needle 15 is drawn out of the insertion means 5. The septum 58 is closed, and the insertion means 5 is ready to insert a medicine into a patient's body.

Figure 23:
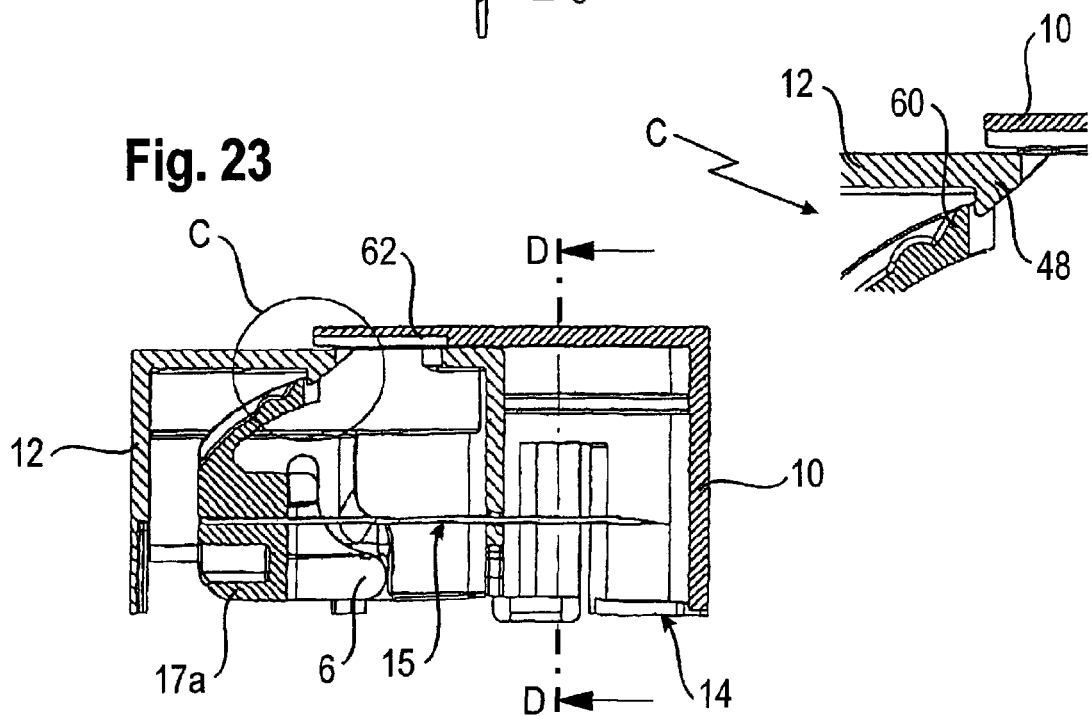
FIG. 23 is a sectional representation of the additional handle component and the movable handle component, after the movable handle component has been drawn out of the additional handle component, with an enlarged detail of area C shown at right.
Figure 23A:
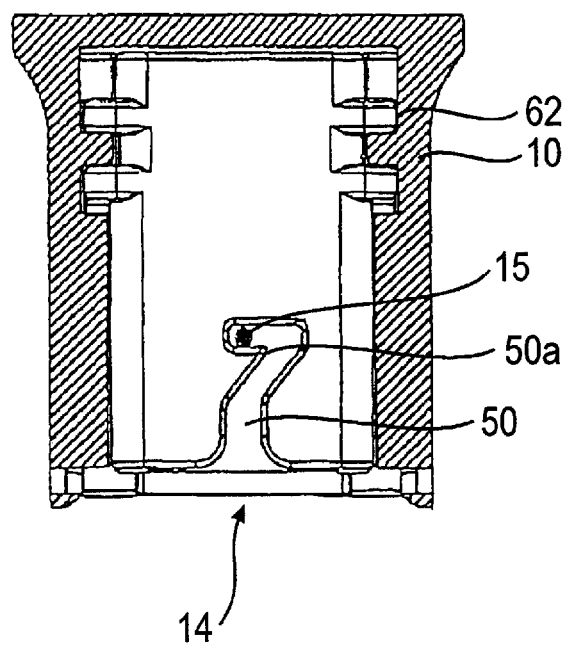
FIG. 23a is a section D-D in accordance with FIG. 23, which is arranged perpendicular to the section in accordance with FIG. 23.

FIG. 23 shows how the movable handle component 12 has been drawn back out of the additional handle component 10, such that the cannula casing 17b has been pivoted back again into its position associated with the protective position. The injection means 15 can be moved via the original protective position into a position above the protective position, i.e. above a latching collar 60 which is explained below. In this position, the injection means 15 is secured, as can be seen in the enlarged image at the right of FIG. 23, by a latching collar 60 at the end of the needle holder 17a passing into engagement with the engaging element 48. In this position, it is then no longer possible to deflect the contaminated injection means 15 out of the handle 10, 12 again, because a locking effect is provided by the engaging element 48 in conjunction with the latching collar 60. The injection means 15 is held behind the latching collar in a locking position. FIG. 23a reproduces a section D-D in accordance with FIG. 23 and depicts a securing link 50 which serves to transfer the used or contaminated injection means 15 into a secured link portion behind a securing collar 50a. An unused, sterile injection means can conversely be held in a different position in front of the securing collar 50a before it is used.

The sectional representation in accordance with FIG. 23a also shows guides 62 which enable the movable handle component 12 to be guided within the additional handle component 10. If the injection means 15 is pivoted back into an inactive position in the receptacle, it is moved, e.g., by flexibly deforming, through the securing link 50, in order to then be positioned in the upper region of the securing link 50 behind the securing collar 50a in order to then securely remain in a blocked position.

Figure 24:
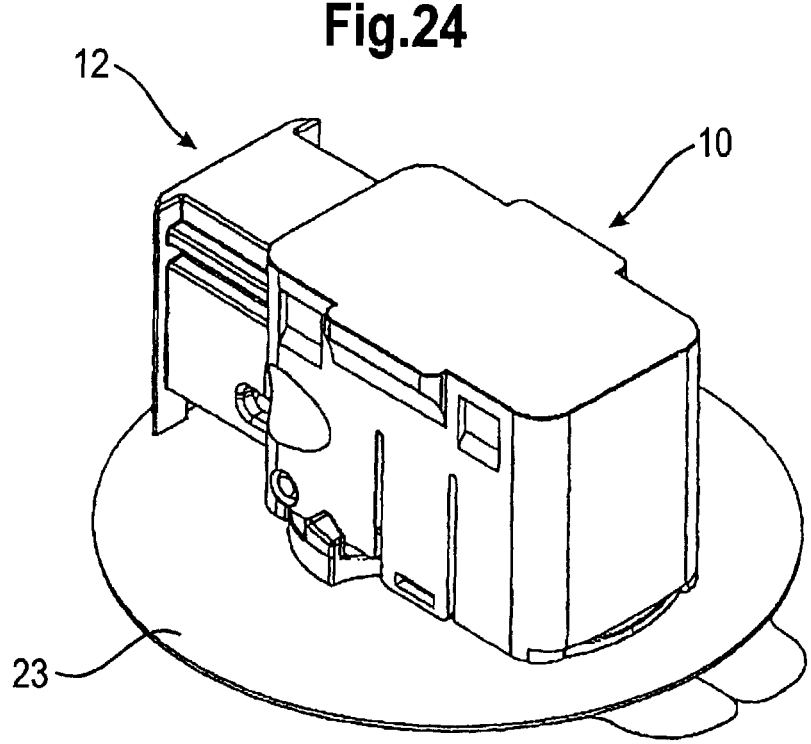
FIG. 24 is an insertion head in accordance with the invention, in a perspective view, before the application.
Figure 25:
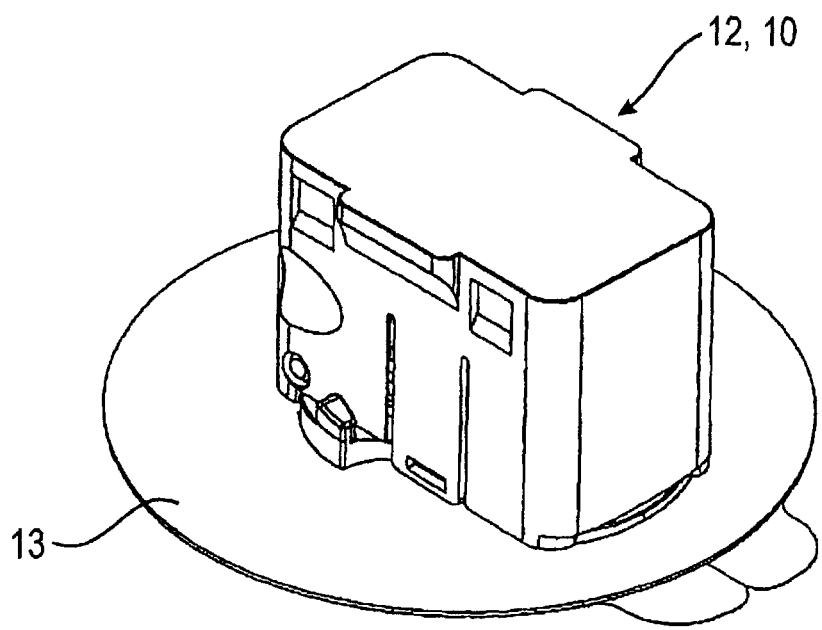
FIG. 25 is the insertion head in accordance with FIG. 24, after the application.
Figure 26:
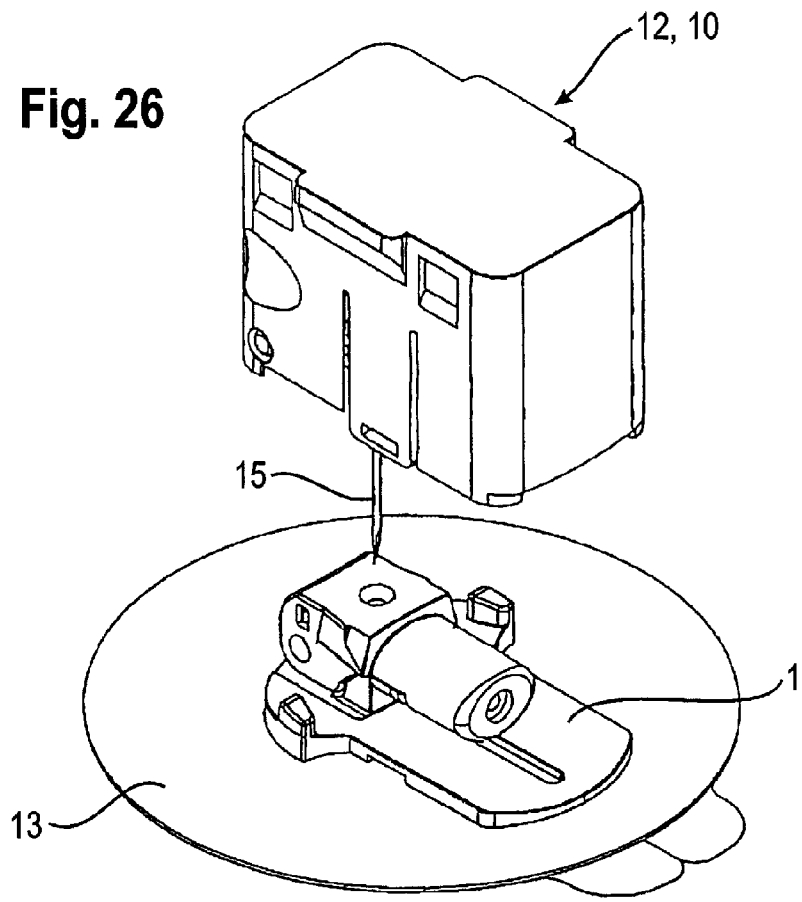
FIG. 26 is the insertion head in accordance with FIGS. 24 and 25, after the additional handle component and the movable handle component together with the injection needle have been removed.

FIGS. 24 to 28 show different stages of the application of an insertion head in accordance with the invention. FIG. 24 shows the movable handle component 12 in a position protruding from the additional handle component 10, in which the insertion means 5 together with the injection needle 15 are in their protective position. In the representation in accordance with FIG. 25, the movable handle component 12 has been moved into the additional handle component 10, such that, as is shown by FIG. 26, the insertion means together with the injection means can be injected into a patient's body. FIG. 26 then shows the state according to which the insertion means together with the injection means 15 has been injected into a patient's body, where the injection means 15 then has no further function and can be drawn out of the insertion means, i.e. the base 1 and the handle 10, 12 can be separated.

Figure 27:
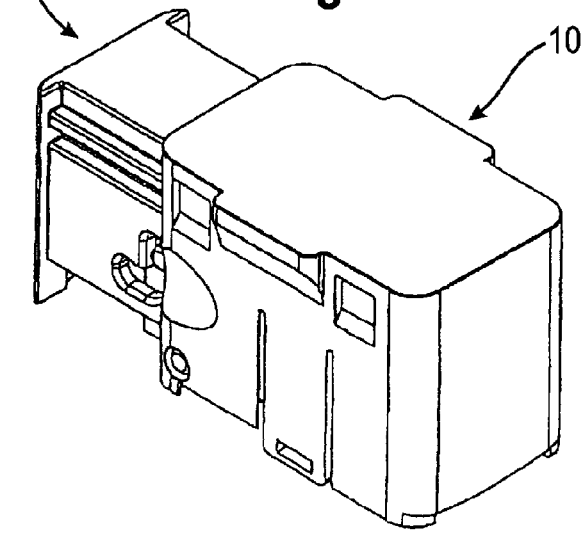
FIG. 27 is the additional handle component and the movable handle component in a perspective view, after the movable handle component has been drawn out of the additional handle component.

In FIG. 27, the movable handle component 12 has then been drawn out of the additional handle component 10, where the injection means 15 has been transferred back into a protective position.

Figure 28:
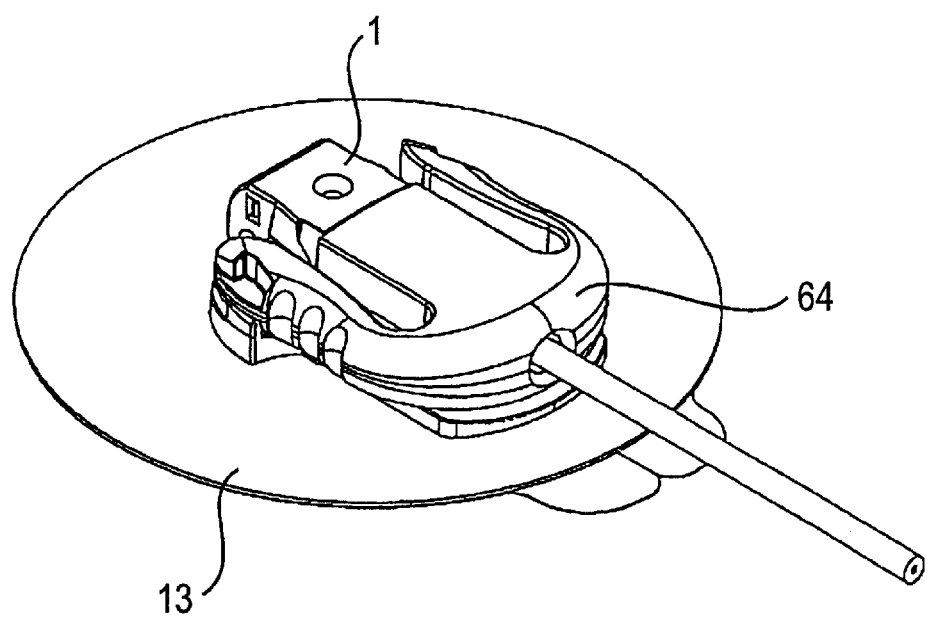
FIG. 28 is the base of the insertion head according to FIGS. 24 to 27, after a connector for supplying a medicine has been docked.

In FIG. 28, a connector 64 comprising a supply conduit can then be docked with the base 1, in order to supply a medicine, for example insulin.

Figure 29:
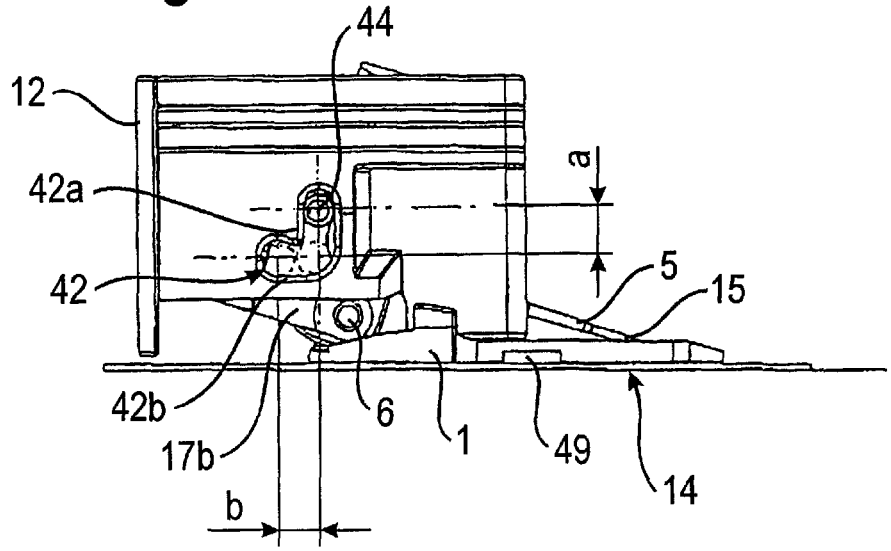
FIG. 29 is an insertion head with the insertion means together with the injection needle situated in the protective position, shown without the additional handle component.

FIG. 29 shows that the link guide 42 has a first portion 42a of length a. This path a serves to pivot the cannula casing 17b and with it the insertion means 5 together with the injection means 15 to the right as shown, by operating or advancing the movable handle component 12, such that the link block 44 is moved downwards towards the joint element 6, while the insertion means 5 is transferred from the protective position into the application position or insertion position. A second portion 42b of the link guide 42 is provided in order to create a clearance over the second path b, in order to enable unlatching in order to be able to deflect the connecting means 16b out of the engagement cavity 49.

Figure 30:
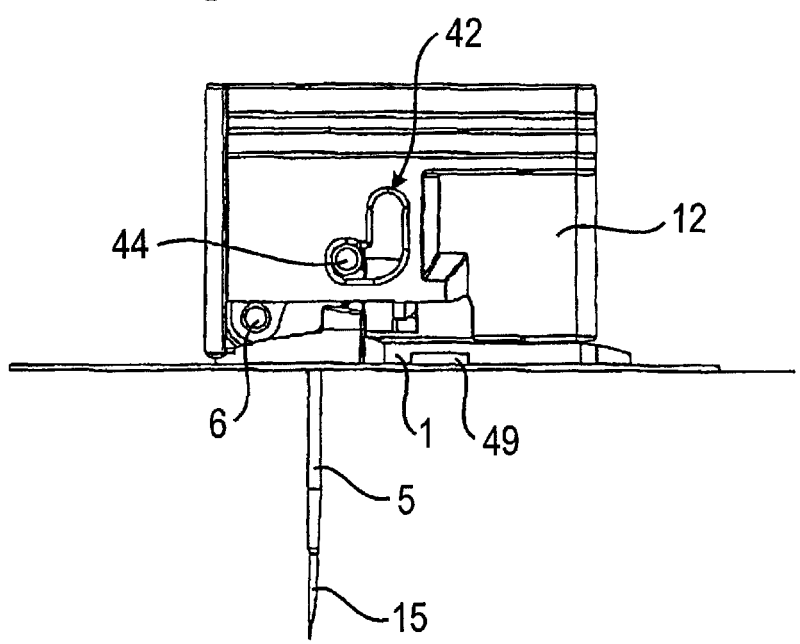
FIG. 30 is the insertion head in accordance with FIG. 29, with the insertion means together with the injection needle in the application position.

Correspondingly in FIG. 30, in which the link block 44 has reached the other end of the link guide 42 relative to the representation in accordance with FIG. 29, the insertion means 5 together with the injection means 15 is not only in its application position, but the handle 10, 12 has also already been unlatched from the base 1 and can be drawn off, where the injection means 15 is drawn out of the insertion means 5.

Figure 31:
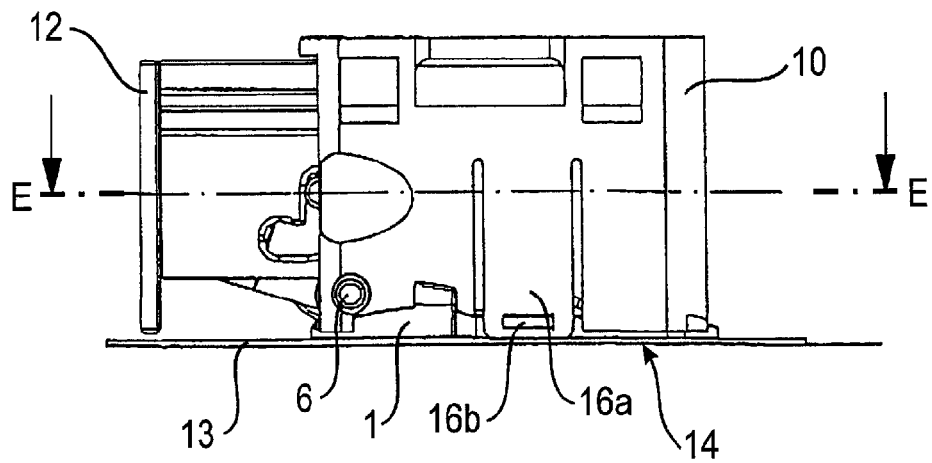
FIG. 31 is an insertion head with the insertion means situated in the protective position, in a lateral view.
Figure 32:
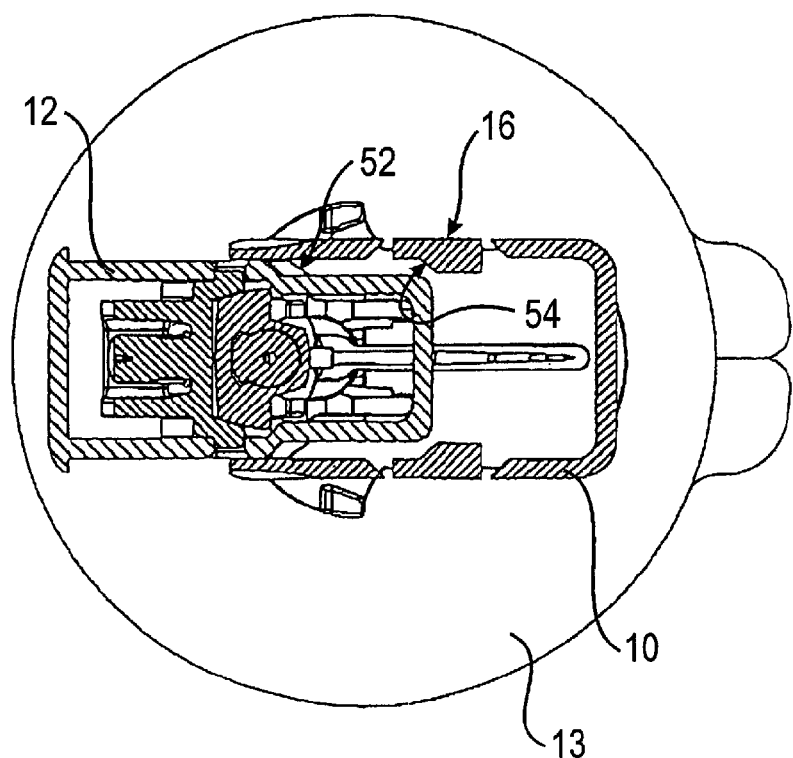
FIG. 32 is a section E-E through the insertion head in accordance with FIG. 31, in a top view.

An unlatching mechanism is additionally shown in the embodiment in accordance with FIG. 31, as shown by the section E-E reproduced in FIG. 32. As can be seen, the movable handle component 12 comprises a control ramp which moves against a deflecting ramp 54 once the movable handle component 12 has been inserted into the additional handle component 10, so as to convey the connecting element 16 out of its engagement with the engagement cavity 49 on the base 1. While the movement for pivoting the insertion means 5 together with the injection means 15 corresponds to the path 42a having the length a, the movement for guiding the control ramp 52 against the deflecting ramp 54 corresponds to the portion 42b of the link guide 42 in accordance with FIG. 29.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An insertion head for medical or pharmaceutical applications to tissue, said insertion head comprising:
   a base comprising a lower side which can be positioned on the tissue,
   an insertion means and an injection means which are both pivotally mounted to the base and can be inserted into the tissue,
      wherein the insertion means and the injection means are configured to pivot relative to the base from a protective position in which a free end of the insertion means is short of the lower side of the base, into an insertion position in which the free end protrudes beyond the lower side,
   a detachable receptacle which is open towards the lower side of the base and is configured to be detached from the base, and which accommodates at least the free end of the insertion means in its protective position,
   wherein the detachable receptacle comprises a handle, the handle comprises a movable handle component movable relative to the base, said movable handle component being coupled to the insertion means such that a movement of the movable handle component relative to the base generates the movement of both the insertion means and injection means from the protective position to the insertion position,
   wherein the handle comprises an additional handle component detachably coupled to the base and immovable relative to the base when coupled such that the movable handle component can be moved against the additional handle component, and a joint element arranged as a shaft of a rotary joint, and with a rotational axis as a joint axis providing the pivot for both the insertion means and the injection means.

2. The insertion head according to claim 1, wherein the base further comprises an additional receptacle which is open towards the lower side of the base and accommodates a portion of the insertion means in its insertion position, wherein the insertion means protrudes through a cavity in the additional receptacle, into the detachable receptacle.

3. The insertion head according to claim 2, wherein the detachable receptacle lengthens the additional receptacle in the longitudinal direction of the insertion means and accommodates the additional receptacle.

4. The insertion head according to claim 2, wherein the additional receptacle comprises an outer surface which slopes outwards in a round bulge from its upper side towards the lower side of the base.

5. The insertion head according to claim 2, wherein the handle comprises a handle part which protrudes from an upper side of the base, and the additional receptacle projects in the longitudinal direction of the insertion means wherein the longitudinal direction is determined when the insertion means is situated in the protective position and the insertion means points parallel or substantially parallel to the lower side of the base, and the additional receptacle extends laterally beyond a perimeter of the handle part in a direction moving from the insertion means to a tip of the injection means and wherein a portion of the base extends beyond the perimeter of the handle part in an approximately opposite direction to the direction of the lateral extension of the additional receptacle.

6. The insertion head according to claim 1, wherein the handle forms the detachable receptacle.

7. The insertion head according to claim 1, wherein the handle comprises a connection between the base and the handle is released when the movable handle component is moved.

8. The insertion head according to claim 7, wherein a first connecting element and a second connecting element are in an engagement which creates the connection, and the movable handle component contacts one of the connecting elements when it is moved, and moves it out of the engagement, against an elasticity force.

9. The insertion head according to claim 1, wherein the handle protrudes from an upper side of the base.

10. The insertion head according to claim 9, wherein a first connecting element is arranged on the base, and a second connecting element is arranged on the handle, wherein the connecting elements are in an engagement which creates the connection, and at least one of the connecting elements can be moved out of the engagement, against an elasticity force.

11. The insertion head according to claim 1, wherein the movable handle component is coupled to the insertion means by means of a transmission.

12. The insertion head according to claim 11, wherein transmission couples the movable handle component to the insertion means by means of a toothed engagement, wherein the toothed engagement comprises a toothed wheel and a toothed rod.

13. The insertion head according to claim 1, wherein the movable handle component is coupled to a toothed rod arranged on the movable handle component, and the insertion means is coupled to a toothed wheel, which is in toothed engagement with the toothed rod.

14. The insertion head according to claim 1, wherein the insertion means is non-rotationally coupled to a toothed wheel which is configured to rotate about the rotational axis.

15. The insertion head according to claim 1, wherein the movable handle component is configured to be shifted relative to the base.

16. The insertion head according to claim 1, wherein the movable handle component is configured to be linearly guided.

17. The insertion head according to claim 1, wherein the movable handle component is configured to be moved at least parallel to the lower side of the base.

18. The insertion head according to claim 1, further comprising a securing link associated with the movable handle component, wherein said movable handle component accommodates the insertion means in the protective position, and wherein the insertion means can be latched into said securing link in the protective position.

19. The insertion head according to claim 1, wherein the movable handle component and the additional handle component are configured such that they can be gripped between two fingers of a hand, wherein with each finger pressing against one of the handle components, the movable handle component can be moved against the additional handle component.

20. The insertion head according to claim 1, wherein the movable handle component is configured to be shifted far enough into the additional handle component that, once the process for transferring the insertion means from the protective position into the insertion position has been completed, a control ramp on the movable handle component abuts against a deflecting ramp on a connecting element which reversibly connects the base to the handle, and deflects out of an engagement position, such that the handle and the base can be separated.

21. The insertion head according to claim 1, wherein the receptacle and the additional handle component comprise one piece.

22. The insertion head according to claim 1, wherein the insertion means is associated with a holding structure which is moved with the insertion means, wherein the holding structure comprises a latching collar which, when the movable handle component is drawn out of the additional handle component, enters into a latching engagement with an engaging element on the movable handle component, in order to prevent the injection means from pivoting out again.

23. The insertion head according to claim 1, wherein the insertion means is associated with a holding structure which is moved with the insertion means, wherein the holding structure comprises a securing structure which opposes a wall of the movable handle component which extends parallel to the movement direction of the movable handle component, wherein an engaging element on the inner side of this wall is in reversible engagement with the securing structure when the insertion means is in its protective position.

24. The insertion head according to claim 1, wherein the insertion means is held on the base via a rotational axis, wherein a link block is provided which is arranged non-centrically in relation to the rotational axis, wherein a link guide is provided which co-operates with the link block; and wherein a movement of the movable handle component relative to the base over a first path of a first portion of the link guide transfers the link block, guided by the link guide, from a first position which corresponds to the protective position of the insertion means, into a second position which corresponds to the insertion position of the insertion means.

25. The insertion head according to claim 24, wherein a connecting means is provided which reversibly connects the base to the handle, wherein in order to detach the handle from the base, the movable handle component is movable over a second path perpendicular to the extending direction of the insertion means situated in the insertion position, wherein the link guide comprises a second portion corresponding to the second path.

26. The insertion head according to claim 1, wherein the movable handle component can be shifted far enough into the additional handle component that, once the process for transferring the insertion means from the protective position into the insertion position has been completed, a control ramp on the movable handle component abuts against a deflecting ramp on a connecting element which reversibly connects the base to the handle, and deflects out of an engagement position, such that the handle and the base can be separated.

27. The insertion head according to claim 1, wherein the insertion means is associated with a holding structure which is moved with the insertion means, wherein the holding structure comprises a latching collar which, when the movable handle component is moved relative to the additional handle component, enters into a latching engagement with an engaging element, in order to prevent the injection means from pivoting out again.

28. The insertion head according to claim 1, wherein the insertion means is flexible and is stabilized by the injection means.

29. The insertion head according to claim 28, wherein the injection means is coupled to the detachable receptacle when the insertion means is moved into the insertion position.

30. The insertion head according to claim 1, wherein the insertion means is elongated in a longitudinal direction, and the longitudinal direction and the lower side of the base enclose an acute angle of less than 50° when the free end of the insertion means protrudes beyond the lower side as it moves into the insertion position.

31. The insertion head according to claim 1, wherein a securing link is provided in the receptacle accommodating the insertion means in the protective position.

32. The insertion head according to claim 31, wherein the securing link can be moved into a locking position which is associated with the insertion means and is close to the protective position.

33. The insertion head according to claim 32, wherein a latching collar is associated with the locking position.

34. The insertion head according to claim 1, wherein the insertion means is associated with a securing structure which reversibly secures the insertion means in the protective position.

35. The insertion head according to claim 34, wherein the insertion means is associated with a cannula casing which is moved with the insertion means, wherein the cannula casing comprises a securing structure which opposes a wall of the movable handle component which extends parallel to the movement direction of the a second handle component, wherein an engaging element on the inner side of this wall is in reversible engagement with the securing structure when the insertion means is in its protective position.

36. An insertion head for medical or pharmaceutical applications to tissue, the insertion head comprising:

a base having an underside which can be placed on the tissue, wherein the base has a receiving portion and a flat portion which are shaped in one piece, an insertion means and an injection means which are configured to pivot relative to the base and can be inserted into the tissue, wherein the insertion means is movable relative to the base from a protection position in which a free end of the insertion means is set back behind the underside of the base into an introduction position in which the free end of the insertion means projects beyond the underside of the base, a detachable receptacle which is open towards the underside of the base and is configured to be detached from the base and which receives at least the free end of the insertion means in the protection position thereof, wherein the detachable receptacle comprises a handle is releasably connected to the base, the handle having a handle portion which projects up from a top side of the base and the detachable receptacle projects laterally from the handle portion, wherein the base and a joint element together form a joint and the insertion means projects from the joint element.

37. The insertion head according to claim 1, wherein both the injection means and the insertion means protrude through the joint element which is coupled to a supply for a medicinal fluid roughly at a right angle to the insertion means.

\* \* \* \* \*

UNITED STATES PATENT AND TRADEMARK OFFICE
CERTIFICATE OF CORRECTION

Page 1 of 1

PATENT NO. : 8,535,269 B2
APPLICATION NO. : 12/049118
DATED : September 17, 2013
INVENTOR(S) : Simon Scheurer et al.

It is certified that error appears in the above-identified patent and that said Letters Patent is hereby corrected as shown below:

In the Specification:

Col. 5, Line 64, "rights angles" should read --right angles--;

Col. 10, Line 62, "FIG. 21 is the insertion head in accordance with FIG. 20A" should read --FIG. 21 is the insertion head in accordance with FIG. 20--;

Col. 11, Line 6, "FIG. 23B is an enlarged detail of area C from FIG. 23A" should read --FIG. 23B is an enlarged detail of area C from FIG. 23--;

Col. 20, Line 14, "41 id" should read --41 is--;

Col. 20, Line 41, "may disposed of" should read --may be disposed of--;

In the Claims:

Col. 27, Claim 35, Line 22, "of the a second handle component" should read --of the second component--; and Col. 28, Claim 36, Line 16, "a handle is releasably" should read --a handle releasably--.

Signed and Sealed this
Twenty-second Day of July, 2014

Michelle K. Lee
*Deputy Director of the United States Patent and Trademark Office*